(12) United States Patent
Yao et al.

(10) Patent No.: US 10,472,640 B2
(45) Date of Patent: Nov. 12, 2019

(54) METHOD OF REAL-TIME PROGNOSIS OF FLOODING PHENOMENON IN PACKED COLUMN

(71) Applicants: NATIONAL TSING HUA UNIVERSITY, Hsinchu (TW); Chang Chun Plastics Co., Ltd., Taipei (TW); Chang Chun Petrochemical Co., LTD., Taipei (TW)

(72) Inventors: Yuan Yao, Hsinchu (TW); Bo-Fan Hseuh, Hsinchu (TW)

(73) Assignees: NATIONAL TSING HUA UNIVERSITY, Hsinchu (TW); Chang Chun Plastics Co., Ltd., Taipei (TW); Chang Chun Petrochemical Co., LTD., Taipei (TW)

( * ) Notice: Subject to any disclaimer, the term of this patent is extended or adjusted under 35 U.S.C. 154(b) by 196 days.

(21) Appl. No.: 15/710,849

(22) Filed: Sep. 21, 2017

(65) Prior Publication Data
US 2018/0265878 A1    Sep. 20, 2018

(30) Foreign Application Priority Data
Mar. 14, 2017 (TW) .............................. 106108393 A

(51) Int. Cl.
*C12N 15/70* (2006.01)
*C12N 15/09* (2006.01)
(Continued)

(52) U.S. Cl.
CPC ............. *C12N 15/70* (2013.01); *C07H 17/08* (2013.01); *C12N 15/09* (2013.01); *C12Q 1/18* (2013.01); *C12R 1/465* (2013.01)

(58) Field of Classification Search
CPC ...................................................... C12N 15/70
See application file for complete search history.

(56) References Cited

U.S. PATENT DOCUMENTS

| 4,511,435 A | 4/1985 | Strohschein |
| 6,891,061 B1 | 5/2005 | Nishimura et al. |

FOREIGN PATENT DOCUMENTS

| CN | 102539523 A | 7/2012 |
| CN | 101765454 B | 7/2013 |

(Continued)

OTHER PUBLICATIONS

English Translation of CN104359503, 2015. (Year: 2015).*
(Continued)

*Primary Examiner* — Matthew D Krcha
(74) *Attorney, Agent, or Firm* — CKC & Partners Co., LLC

(57) ABSTRACT

A method of real-time prognosis of a flooding phenomenon in a packed column includes steps as follows. An online data collection step is conducted, wherein a plurality of values of the pressure drop are collected from the packed column under operation. A calculation step is conducted, wherein the values of the pressure drop are used to calculate a plurality of values of a steadiness index. A statistical step is conducted, wherein a value of a monitoring statistic is calculated based on the values of the steadiness index. A control step is conducted, wherein the value of the monitoring statistic is compared to a control limit, and an alarm is triggered when the value of the monitoring statistic is greater than the control limit.

16 Claims, 22 Drawing Sheets

(51) Int. Cl.
  *C12R 1/465* (2006.01)
  *C12Q 1/18* (2006.01)
  *C07H 17/08* (2006.01)

(56) References Cited

FOREIGN PATENT DOCUMENTS

| CN | 104359503 A | * | 2/2015 |
|---|---|---|---|
| CN | 104359503 A | | 2/2015 |
| EP | 0995958 A2 | | 4/2000 |

OTHER PUBLICATIONS

T. K. Sherwood et al., "Flooding Velocities in Packed Columns", Industrial & Engineering Chemistry, published on Jul. 1, 1938, vol. 30, issue 7, pp. 765-769, published by American Chemical Society, Unites states.

J. C. Elgin et al., "Liquid Holdup and Flooding in Packed Towers", Industrial & Engineering Chemistry, published on Apr. 1, 1939, vol. 31, issue 4, pp. 435-445, published by American Chemical Society, Unites states.

Sanjay Parthasarathy et al., "Prediction of Flooding in an Absorption Column using Neural Networks", Proceedings of the 1999 IEEE International Conference on Control Applications, dated on Aug. 22-27, 1999, vol. 2, pp. 1056-1061, Unites states.

Vladimir Jiřičný et al., "Experimental Study of the Flooding and Appearance of a Bubble Bed on Top of a Countercurrent Packed-Bed Column", Industrial & Engineering Chemistry Research, published on Jan. 10, 2001, vol. 40, issue 1, pp. 407-412, published by American Chemical Society, Unites states.

Erin Hansuld et al., "Acoustic detection of flooding in absorption columns and trickle beds", Chemical Engineering and Processing: Process Intensification, published in May 2008, vol. 47, issue 5, pp. 871-878, published by Elsevier B.V., Netherlands.

* cited by examiner

METHOD OF REAL-TIME PROGNOSIS OF FLOODING PHENOMENON IN PACKED COLUMN

RELATED APPLICATIONS

This application claims priority to Taiwan Application Serial Number 106108393, filed Mar. 14, 2017, which is herein incorporated by reference.

BACKGROUND

Technical Field

The present disclosure relates to a method of real-time prognosis of a flooding phenomenon in a packed column. More particularly, the present disclosure relates to a method of real-time prognosis of a flooding phenomenon in a packed column which adopts a statistical process control (SPC) method.

Description of Related Art

In chemical industries, a packed column is a separation apparatus utilized in a gas-liquid system. The packed column is capable to achieve high mass transfer rates even in the situations of strong flow fluctuations and relatively low pressure drop, and thus is widely used. However, when a relative flow rate of a gas and a liquid exceeds an extreme limit, the pressure drop in the packed column increases sharply, which hinders the liquid from flowing downwardly. Instead, the liquid spills out from the top of the packed column, which is a common error of the packed column and is called a flooding phenomenon. The flooding phenomenon lowers the purity of the products, interferes the normal operation of process, and even shuts down the entire production line which results in a huge loss.

In general, the higher the gas flow rate and/or the liquid flow rate, the higher the operational efficiency can be obtained. In other words, the packed column can reach the highest efficiency when the operational condition is close to the flooding point (the critical gas flow rate at which the flooding phenomenon occurs). However, in practice, the gas flow rate is conservatively set at about 0.6 to 0.8 of the flooding point for the sake of safety. The flooding phenomenon can be prevented effectively, but drawbacks, such as low production rate and high energy consumption, are results. How to precisely predict or judge the flooding point for both high efficiency and operational safety is the goal of relevant industry.

The conventional methods for predicting or judging the flooding point adopt empirical correlations and models, and the prediction accuracy thereof depends on empirical parameters related to the packed column under consideration. However, different packed columns have different empirical parameters. It is difficult to obtain the empirical parameters when the design of the packed column is unknown. Considering the fact that numerous types of the packed columns are used in industry, it is difficult to obtain the empirical parameters of all the packed columns. Also, the existing empirical parameters obtained from a specific packed column are hardly adequate for other packed columns. Consequently, the conventional methods for predicting or judging the flooding point by adopting empirical correlations and models cannot predict the flooding point precisely.

For avoiding the drawbacks of the empirical correlations and models which require a large number of history data, methods of real-time monitoring are developed. The most direct method for real-time monitoring is visual inspection, i.e., observing the heaping phenomenon of liquid upon the surface of packings via human eyes. However, visual inspection only can be applied to the packed column with transparent column body. Moreover, delay is also a problem. When the flooding phenomenon is observed by human eyes, the error has already occurred. Even if the operational conditions of the packed column are adjusted immediately, it still requires a period of time for the process to return to normal.

Other methods of real-time prognosis of flooding points were developed. The process variables, such as pressure drops, flow rates and temperatures, can be measured in real-time via sensing and transmitting elements. A plenty of process information can be obtained by analyzing the measured data of the process variables, which represents the status of operational conditions. If the operational status can be recognized from the process information, a proper adjustment can be made before or at the moment that the error occurs. Accordingly, unnecessary loss can be avoided. For example, Dzyacky monitors a plurality of process variables, such as temperatures, pressure drops and flow rates, and a threshold value of each of the process variables corresponding to normal condition is set. When multiple process variables are greater than the threshold values, the possibility of flooding phenomenon is asserted. However, with the change of the flow rate, it is difficult to establish accurate threshold values. Moreover, if the correlations between different process variables are neglected, Type I errors may occur. In another example, Hansuld et al. discloses a method of real-time prognosis of flooding points by measuring acoustic wave signals. Specifically, a plurality of receptors of the acoustic wave signals are installed on the external surface of the column body for collecting the acoustic wave signals of the liquid inside the packed column. The flooding point is detected by analyzing the change of the acoustic wave signals. Although the method can assist the engineer to judge the operational status inside the packed column, there still lacks effective SPC methods to determine a control limit. The definitions of the operational status and the threshold values are still dependent on human decisions.

Given the above, the developed methods for prognosis of flooding point have drawbacks of requiring a number of empirical parameters to establish the model, lacking the necessary ability of providing accurate judgement, excessively depending on human decisions, lacking the necessary ability of being applied to all types of packed columns or requiring invasively modifying the packed column, and thus can hardly be used in industry. Therefore, there still needs a method of real-time prognosis of flooding points which has advantages of being capable of being applied to all types of packed columns and providing accurate judgement, and not depending on human decisions.

SUMMARY

According to one embodiment of the present disclosure, a method of real-time prognosis of a flooding phenomenon in a packed column includes steps as follows. An online data collection step is conducted, wherein a plurality of values of a pressure drop are collected from the packed column under operation. A calculation step is conducted, wherein the values of the pressure drop are used to calculate a plurality of values of a steadiness index. A statistical step is conducted, wherein a value of a monitoring statistic is calculated based on the values of the steadiness index. A control step is conducted, wherein the value of the monitoring statistic is compared to a control limit, and an alarm is triggered when the value of the monitoring statistic is greater than the control limit.

According to another embodiment of the present disclosure, a method of real-time prognosis of a flooding phenomenon in a packed column includes steps as follows. An online data collection step is conducted, wherein a plurality of values of a pressure drop are collected from the packed column under operation. A calculation step is conducted, wherein the values of the pressure drop are used to calculate a value of a steadiness index. A control step is conducted, wherein the value of the steadiness index is compared to a control limit, and an alarm is triggered when the value of the steadiness index is greater than the control limit.

BRIEF DESCRIPTION OF THE DRAWINGS

The present disclosure can be more fully understood by reading the following detailed description of the embodiments, with reference made to the accompanying drawings as follows.

DETAILED DESCRIPTION

According to the present disclosure, different algorithms/formulas may use identical symbols, and definitions of the identical symbols may be the same or different. The definition of each of the symbols is defined by its corresponding algorithm/formula.

According to the present disclosure, the term "pressure drop" is a noun, and a value of the pressure drop is a numerical value for describing the quantity of the pressure drop.

According to the present disclosure, the term "monitoring statistic" is a noun, and a value of the monitoring statistic is a numerical value for describing the quantity of the monitoring statistic.

According to the present disclosure, the term "steadiness index" is a noun, and a value of the steadiness index is a numerical value for describing the quantity of the steadiness index.

Figure 1:
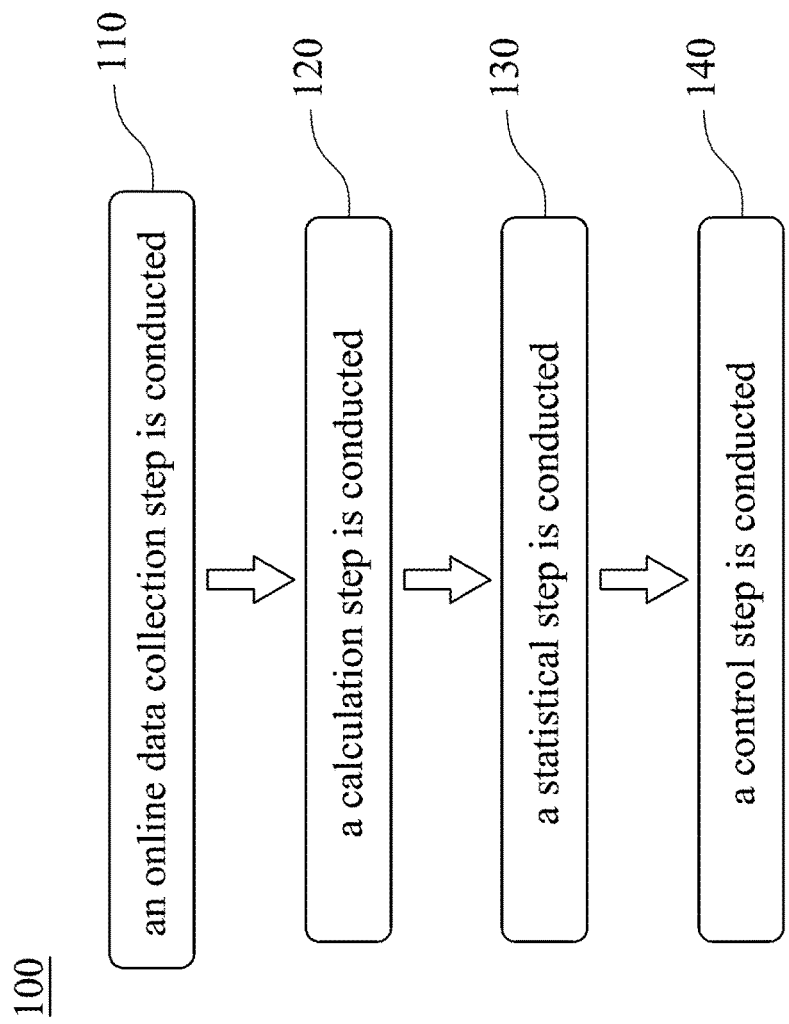
FIG. 1 is a flow diagram showing a method of real-time prognosis of a flooding phenomenon in a packed column according to one embodiment of the present disclosure.

FIG. 1 is a flow diagram showing a method of real-time prognosis of a flooding phenomenon in a packed column 100 according to one embodiment of the present disclosure. In FIG. 1, the method of real-time prognosis of the flooding phenomenon in the packed column 100 includes Step 110, Step 120, Step 130 and Step 140.

In Step 110, an online data collection step is conducted, wherein a plurality of values of a pressure drop are collected from the packed column under operation. Specifically, at least one sensing and transmitting element can be installed in the packed column. The sensing and transmitting element is applied to measure the pressure drop in the packed column, i.e., the sensing and transmitting element is applied to measure values of the pressure drop in the packed column. Furthermore, the sensing and transmitting element can be connected with a computer (via a wired or wireless connection). Thus, the values of the pressure drop measured by the sensing and transmitting element can be delivered to the computer in real time, and can be recorded and calculated by the computer. Moreover, the packed column can further include a blower and a liquid pump. The blower can change a gas flow rate according to an instruction of the computer. Alternatively, the liquid pump can change a liquid flow rate according to the instruction of the computer. Alternatively, the blower can change the gas flow rate and the liquid pump can change the liquid flow rate simultaneously according to the instruction of the computer. For example, when an alarm is triggered, which represents the flooding phenomenon is going to happen, an instruction for reducing the gas flow rate of the packed column can be sent from the computer to the blower, then the blower reduces the gas flow rate of the packed column according to the instruction. Accordingly, the flooding phenomenon can be prevented. The delivery of the data (i.e., the values of the pressure drop) and the instruction between the computer and the packed column, and the record and calculation of the data can be implemented by an input/output signal card and corresponding software installed in the computer. For example, the input/output signal card can be, but is no limited to, NI PXI-8433/4 produced by the National Instruments Corporation, which can be coordinated with corresponding software of LabVIEW produced by the National Instruments Corporation or a self-developed software based on C++ or another programming language.

In Step 120, a calculation step is conducted, wherein the values of the pressure drop are used to calculate a plurality of values of a steadiness index. Each of the values of the steadiness index can be calculated by Formula (1), Formula (2) and Formula (3):

$$S^2 = \frac{\sum_{i=1}^{n}(P_i - \overline{P})^2}{n-1}; \tag{1}$$

$$\frac{\delta^2}{2} = \frac{\sum_{i=1}^{n-1}(P_{i+1} - P_i)^2}{2(n-1)}; \tag{2}$$

$$R = \frac{2S^2}{\delta^2}; \tag{3}$$

wherein R is the steadiness index, $S^2$ is an estimator of a sample variance, $\delta^2/2$ is another estimator of the sample variance, $P_i$ is an ith value of the pressure drop, n is a sample size of the values of the pressure drop, $\overline{P}$ is a sample mean of the values of the pressure drop with the sample size of n, and i is an integral from 1 to n. Specifically, $P_1$, $P_2$, ... and Pn are n number of the values of the pressure drop which are measured continuously. $S^2$ is the estimator of the sample variance of the n number of the values of the pressure drop, and is independent with the measuring sequence of the values of the pressure drop. If there is an unsteady trend in the values of the pressure drop, the $S^2$ will be affected by the unsteady trend. $\delta^2/2$ is another estimator of the sample variance of the n number of the values of the pressure drop, and can minimize the influence of the unsteady trend in the values of the pressure drop. As shown in Formula (3), R is the ratio of the two estimators of the sample variance. The unsteady trend can be quantified by the steadiness index R. Specifically, when the value of the steadiness index R is near 1, there is no unsteady trend in the values of the pressure drop; when the value of the steadiness index R is greater than 1, there is an unsteady trend in the values of the pressure drop. According to the experimental results, when the packed column is under normal operation, the unsteadiness of the trajectory of the pressure drop is below a threshold. However, when the flooding phenomenon is going to happen or is happening, the unsteadiness of the trajectory of the pressure drop increases significantly. Therefore, the steadiness index R can extract useful process information from the pressure drop. In the method according to the present disclosure, the values of the steadiness index R are further calculated to be the criterion of predicting and judging the occurrence of the flooding phenomenon, and details thereof are recited hereinafter.

Figure 2:
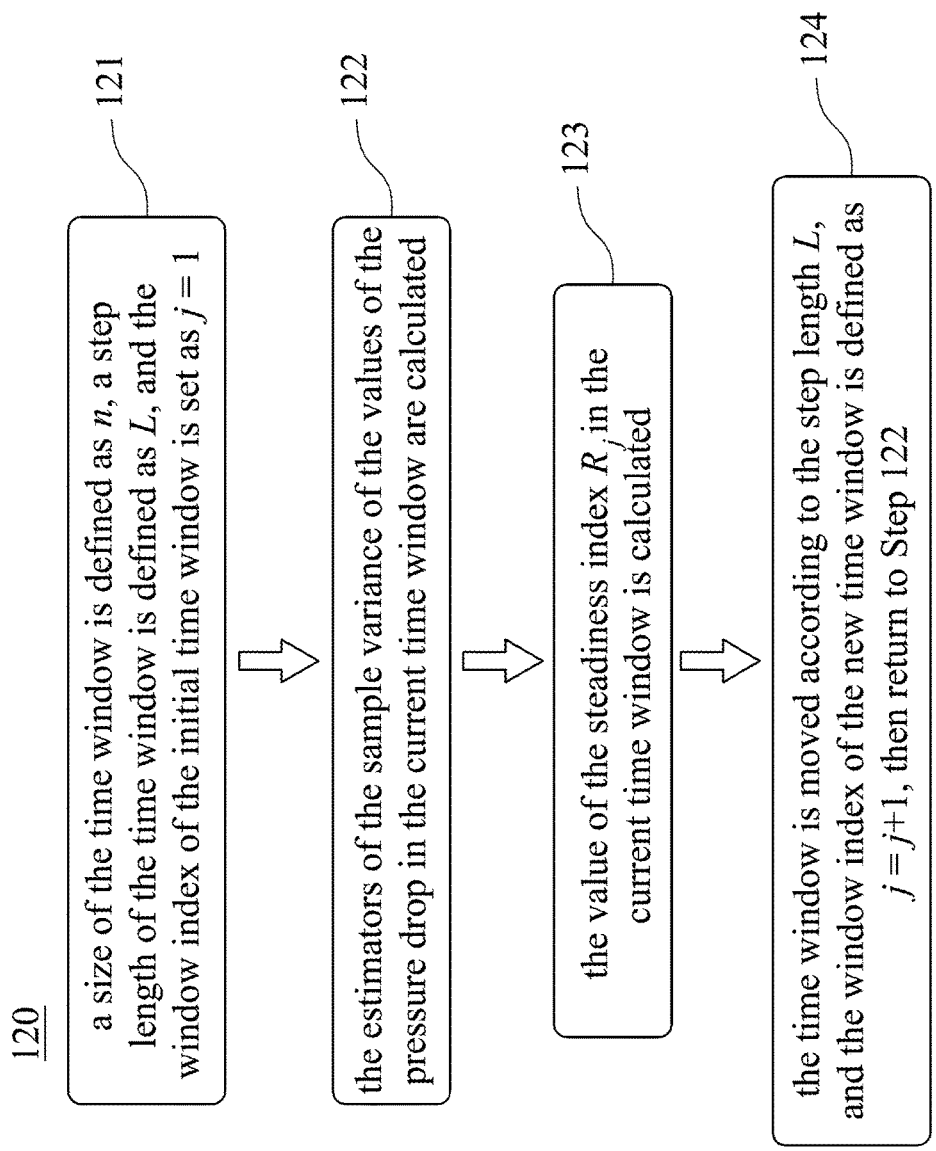
FIG. 2 is a flow diagram showing Step 120 of FIG. 1.

Moreover, in Step 120, the values of the pressure drop used to calculate the values of the steadiness index R can be selected by a method of moving a time widow online (also called "a moving window method"). The following outlines how to calculate the values of the steadiness index R from Formula (1), Formula (2) and Formula (3) with the method of moving the time widow online. FIG. 2 is a flow diagram showing Step 120 of FIG. 1. In FIG. 2, Step 120 includes Step 121, Step 122, Step 123 and Step 124.

In Step 121, a size of the time window is defined as n, a step length of the time window is defined as L, and the window index of the initial time window is set as j=1. As such, the values of the pressure drop to calculate the value of the steadiness index R can be determined. For example, when the size of the time window is defined as 10 (n=10) and the step length of the time window is defined as 2 (L=2), which means 10 continuous values of the pressure drop are selected as the sample to calculate the value of the steadiness index R in the current time window, and the interval between the current time window and the next time window is 2 values of the pressure drop. That is, the 10 continuous values of the pressure drop in the second time window start from the third value of the pressure drop in the first time window, the 10 continuous values of the pressure drop in the third time window start from the fifth value of the pressure drop in the first time window and so on.

In Step 122, the estimators of the sample variance of the values of the pressure drop in the current time window are calculated, that is, $S^2$ and $\delta^2/2$ of the n number of the values of the pressure drop in the current time window (i.e., the time window with the time window index of j) are calculated.

In Step 123, the value of the steadiness index $R_j$ in the current time window is calculated. That is, R is calculated by Formula (3), and its value is named as $R_j$.

In Step 124, the time window is moved according to the step length L, and the window index of the new time window is defined as j=j+1, then return to Step 122.

As shown in FIG. 2, it is favorable for calculating the values of the steadiness index R in real time by the method of moving the time widow online. Specifically, when the online data collection step is conducted, the values of the pressure drop are continuously collected and recorded. By dividing the values of the pressure drop into different time widows and calculating the value of the steadiness index R corresponding to each time window, it is favorable for observing the changing trend of the values of the pressure drop over time and is benefit to achieve the goal of real-time prognosis of the flooding phenomenon. There is a tradeoff between the accuracy and the monitor efficiency in the determination of the size of the time window. Specifically, an increased accuracy can be achieved by increasing the size of the time window, however, the monitor efficiency is decreased. According to one example of the present disclosure, the size of the time window is 20, and the step length of the time window is 1, so that both of the demands of accuracy and monitor efficiency can be satisfied; however, the present disclosure is not limited thereto.

According to another embodiment of the present disclosure, each of the values of the steadiness index can be calculated by Formula (4), Formula (5), Formula (6) and Formula (7):

$$P_{f,i} = \lambda_1 P_i + (1-\lambda_1)P_{f,i-1}; \tag{4}$$

$$S_{f,i}^2 = \lambda_2(P_i - P_{f,i-1})^2 + (1-\lambda_2)S_{f,i-1}^2; \tag{5}$$

$$\delta_{f,i}^2 = \lambda_3(P_i - P_{i-1})^2 + (1-\lambda_3)\delta_{f,i-1}^2; \tag{6}$$

$$R2 = \frac{(2-\lambda_1)S_{f,i}^2}{\delta_{f,i}^2}; \tag{7}$$

wherein R2 is the steadiness index, $P_i$ is an ith value of the pressure drop, $P_{f,i}$ is a filtered value of $P_1$ ($P_{f,i}$ is a value obtained by modifying $P_i$ with an exponentially weighted moving (EWM) filter), $S_{f,i}^2$ is a sample variance (filtered), $\delta_{f,i}^2$ is a mean square successive difference (filtered), and $\lambda_1$, $\lambda_2$ and $\lambda_3$ are the filter parameters. The unsteady trend existing in the values of the pressure drop can be quantified by the steadiness index R2. Specifically, when the value of the steadiness index R2 is near 1, there is no unsteady trend in the values of the pressure drop; when the value of the steadiness index R2 is greater than 1, there is an unsteady trend in the values of the pressure drop. Therefore, the steadiness index R2 can extract useful process information from the pressure drop. In the method according to the present disclosure, the values of the steadiness index R2 can be further calculated to be the criterion of predicting and judging the occurrence of the flooding phenomenon.

Referring back to FIG. 1, in Step 130, a statistical step is conducted, wherein a value of a monitoring statistic is calculated based on the values of the steadiness index (R or R2).

In Step 140, a control step is conducted, wherein the value of the monitoring statistic is compared to a control limit, and an alarm is triggered when the value of the monitoring statistic is greater than the control limit. Moreover, the value of the monitoring statistic and the control limit can be plotted in a control chart. Therefore, it is favorable to directly monitor the flooding phenomenon of the packed column in real time via a graphic presentation. Step 110 to Step 140 can be repeated for continuously monitoring the flooding phenomenon in the packed column.

Specifically, Step 130 and Step 140 can be implemented by a SPC method. The SPC method is a statistical analysis method widely used in industry for monitoring the performance of a manufacturing process, wherein the control limit is determined by analyzing sample data, and the control limit is applied to judge the status of the manufacturing process. In the present disclosure, the values of the steadiness index calculated in different time windows are the sample data of the SPC method. In brief, in the method of real-time prognosis of the flooding phenomenon in the packed column 100, a plurality of values of the steadiness index are collected in advance (which can be the training sample set mentioned below), and the plurality of values of the steadiness index are analyzed to determine a control limit in advance. Afterward, the pre-determined control limit is applied to monitor the value of the steadiness index which is calculated online when the packed column under operation, so that the flooding phenomenon of the packed column can be monitored in real time.

The values of the steadiness index obtained by experiments are tested by a normality test, which indicates the distribution of the values of the steadiness index is not a Gaussian distribution, so that the SPC methods suitable for the present disclosure are the SPC methods irrelevant to the distribution of the sample data (i.e., the SPC methods based on distribution-free charting technique), such as the non-parametric SPC method. The following outlines how to calculate the value of the monitoring statistic from the values of the steadiness index and how to determine the control limit in advance based on a nonparametric SPC method using Mann-Whitney test (hereinafter, MW SPC method). However, the present disclosure is not limited thereto. As mentioned above, the steadiness index can extract useful process information from the pressure drop, i.e., when the packed column is close to the flooding point, a shift (or a changing trend) of the values of the steadiness index can be observed. Therefore, the SPC methods which can detect the shift (or the changing trend) of the values of the steadiness index and are irrelevant to the distribution of the sample data are all suitable for the present disclosure.

The main idea of the MW SPC is as follows. Suppose that a training sample set (also called "reference data") of size m1, $R_X=(R_{X1}, R_{X2}, R_{X3}, \ldots R_{Xm1})$, is collected when the process is in control. In the present disclosure, $R_X$ refers m1 number of the values of the steadiness index which are calculated from the packed column under normal operation. The normal operation refers that the packed column is operated without the flooding phenomenon. Preferably, the normal operation can refer that the packed column is operated when the gas flow rate is in a range below a loading point. Afterward, H sets of test samples are collected. Each of the test sample sets includes m2 number of test data points, and is expressed as $R_Y^h=(R_{Y1}^h, R_{Y2}^h, R_{Y3}^h, \ldots R_{Ym2}^h)$, wherein h denotes the set number, i.e., the hth test sample set, and h is an integer from 1 to H. In the present disclosure, $R_Y^h$ refers m2 number of the values of the steadiness index which are calculated online when the packed column under operation (i.e., are obtained via Step 110 and Step 120). Then the value of the monitoring statistic can be calculated according to MW test (i.e., via Step 130). The value of the monitoring statistic can be calculated by Formula (8):

$$M_{X,Y}^h = \sum_{i=1}^{m1} \sum_{j=1}^{m2} I(R_{Xi} < R_{Yj}^h); \tag{8}$$

In Formula (8), $M_{X,Y}^h$ represents the monitoring statistic, $I(R_{Xi} < R_{Yj}^h)$ is an indicator function for the event of $\{R_{Xi} < R_{Yj}^h\}$. When $\{R_{Xi} < R_{Yj}^h\}$ is valid, $I(R_{Xi} < R_{Yj}^h)$ equals to 1. When $\{R_{Xi} < R_{Yj}^h\}$ is invalid, $I(R_{Xi} < R_{Yj}^h)$ equals to 0. Hence, $M_{X,Y}^h$ is a value between 0 and m1m2.

The value of the monitoring statistic $M_{X,Y}^h$ is compare to a control limit. When the value of the monitoring statistic $M_{X,Y}^h$ is greater than the control limit, which means the flooding phenomenon is happening or is going to happen, and an alarm is triggered (i.e., Step 140).

Figure 3:
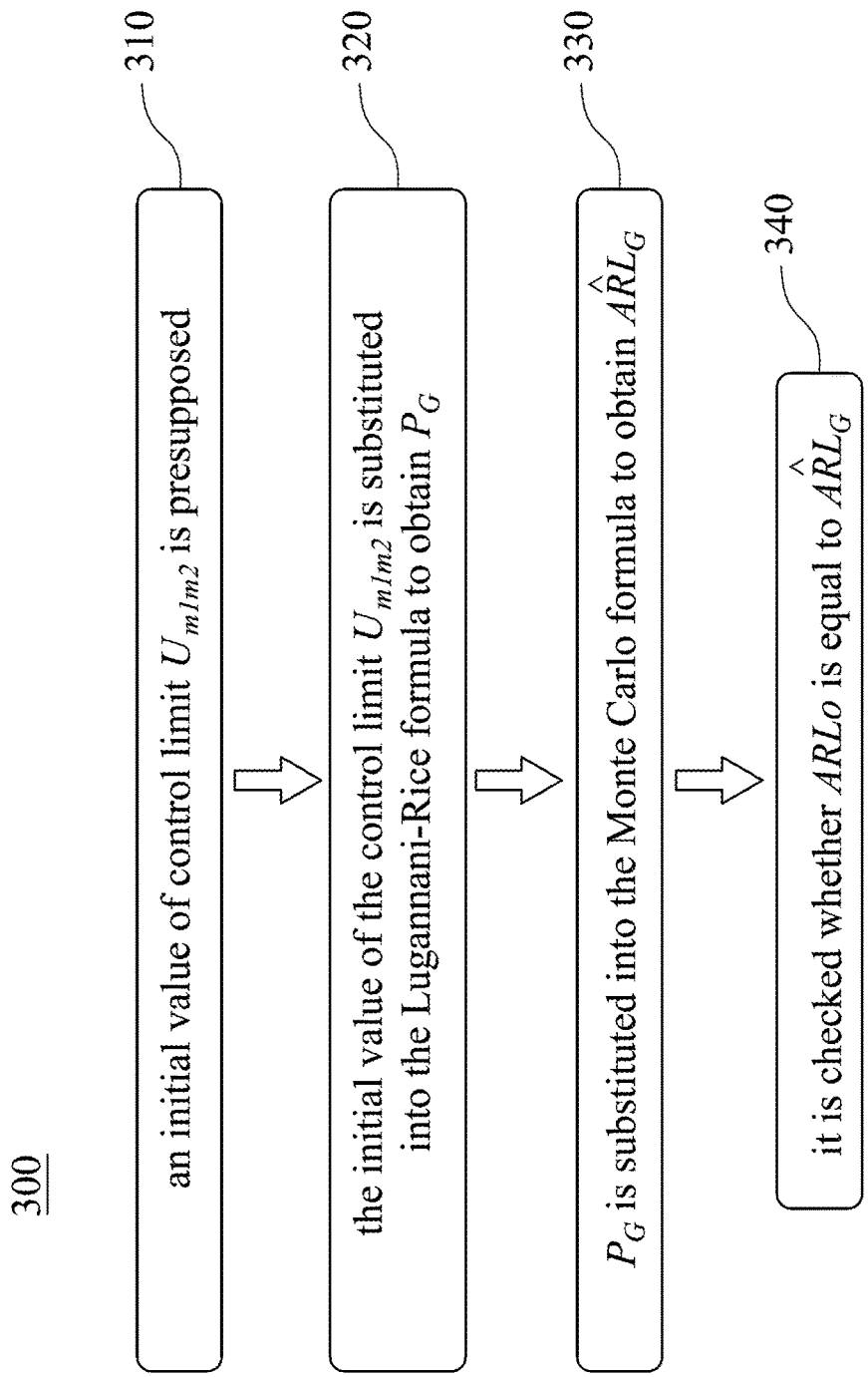
FIG. 3 is a flow diagram showing a method for determining a control limit of FIG. 1.

The control limit is determined before conducting the method of real-time prognosis of the flooding phenomenon in the packed column 100. The control limit is determined by choosing the average run length in control (ARLo), and 370 or 500 is the most commonly chosen value for the ARLo. When the ARLo equals to 370, it means that probability of a false alarm is about 0.27% when the process status is normal. When the ARLo equals to 500, it means that probability of a false alarm is about 0.20% when the process status is normal. When the ARLo, the size of the training sample set m1 and the size of the test sample set m2 are given, the control limit can be determined by the iterative steps of a linear interpolation method. FIG. 3 is a flow diagram showing a method for determining the control limit 300 of FIG. 1. The method for determining the control limit 300 includes Step 310, Step 320, Step 330 and Step 340.

In Step 310, an initial value of control limit $U_{m1m2}$ is presupposed.

In Step 320, the initial value of the control limit $U_{m1m2}$ is substituted into the Lugannani-Rice formula to obtain $P_G$, which is shown in Formula (9):

$$P_G(M_{X,Y}^h > U_{m1m2}) = \tag{9}$$
$$P_G(\overline{M_{X,Y}^h} > U_{m1m2}/m2) = P_G(\overline{M_{X,Y}^h} \geq \mu) \approx 1 - \Phi(r) + \varphi(r)\left(\frac{1}{\lambda} - \frac{1}{r}\right);$$
$$\lambda = m2^{1/2}(1 - e^\gamma)\sigma(\gamma); r = (sgn\gamma)\{2n(\gamma\mu - k(\gamma))\}^{1/2};$$

wherein y is a saddle point, $\Phi(r)$ is a cumulative distribution function of r, and $\varphi(r)$ is a probability distribution function of r.

In Step 330, $P_G$ is substituted into the Monte Carlo formula to obtain $\hat{ARL}_G$, as shown in Formula (10):

$$A\hat{R}L_G \approx \frac{1}{K}\sum_{i=1}^{K}\frac{1}{P_G(X_i)}. \quad (10)$$

In Step 340, it is checked whether ARLo is equal to $\hat{ARL}_G$. When ARLo equals to $\hat{ARL}_G$, the presupposed initial value of the control limit $U_{m1m2}$ is set as the control limit pursued. When ARLo does not equal to $\hat{ARL}_G$, another $U_{m1m2}$ is presupposed and repeat Step 310 to Step 340 till the pursued control limit is obtained.

When ARLo=500 and the size of the test sample set m2=5, the control limits corresponding to different sizes of the training sample set m1 are listed in Table 1, which are the results of calculation.

TABLE 1

| m1 | control limit |
|---|---|
| 50 | 217 |
| 75 | 326 |
| 100 | 435 |
| 150 | 654 |
| 300 | 1304 |
| 500 | 2172 |
| 750 | 3258 |
| 1000 | 4347 |
| 1500 | 6520 |
| 2000 | 8691 |

That is, when ARLo=500, the size of the test sample set m2=5, and the desired size of the training sample set m1 is already recorded in Table 1, the control limit can be obtained simply by looking up Table 1.

To sum up, when the MW SPC method is adopted, the values of ARLo, the size of the training sample set m1 and the size of the test sample set m2 are predetermined for determining the control limit in advance. Then the values of the pressure drop collected online are used to calculate a plurality of values of the steadiness index, followed by the calculation of the monitoring statistic as in Formula (8). The value of the monitoring statistic is compared to the control limit. When the value of the monitoring statistic is greater than the control limit, an alarm is triggered. Furthermore, the size of the training sample set m1 should be selected properly, which allows to reflect the systematic variations in the values of the pressure drop when the packed column is under normal operation. The size of the test sample set m2 should give consideration to both the accuracy and the monitoring efficiency.

Figure 4:
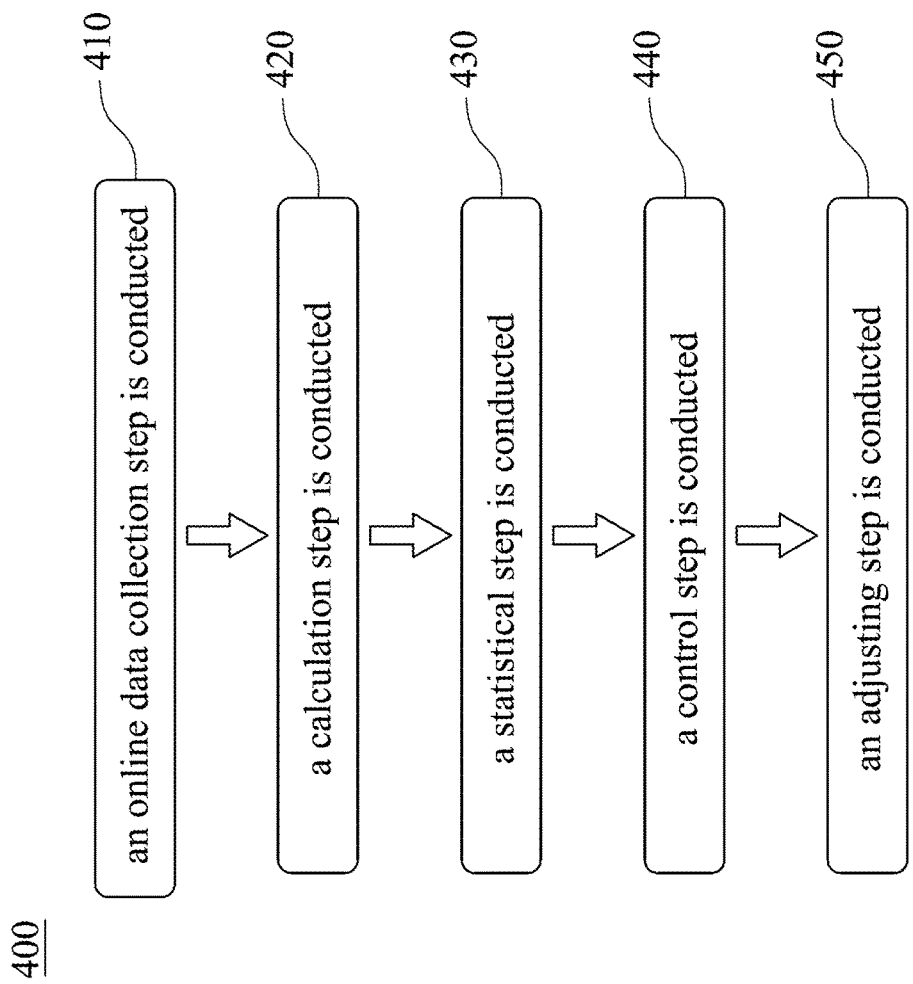
FIG. 4 is a flow diagram showing a method of real-time prognosis of a flooding phenomenon in a packed column according to another embodiment of the present disclosure.

FIG. 4 is a flow diagram showing a method of real-time prognosis of a flooding phenomenon in a packed column 400 according to another embodiment of the present disclosure. In FIG. 4, the method of real-time prognosis of the flooding phenomenon in the packed column 400 includes Step 410, Step 420, Step 430, Step 440 and Step 450.

In Step 410, an online data collection step is conducted. In Step 420, a calculation step is conducted. In Step 430, a statistical step is conducted. In Step 440, a control step is conducted. Details of Step 410 to Step 440 can be the same as that of Step 110 to Step 140 in FIG. 1, and are not repeated herein.

In Step 450, an adjusting step is conducted after the alarm is triggered, wherein an operational condition of the packed column is adjusted to make the value of the monitoring statistic less than the control limit. Specifically, the blower can change a gas flow rate or the liquid pump can change a liquid flow rate according to an instruction of the computer, or the blower can change the gas flow rate and the liquid pump can change the liquid flow rate simultaneously according to the instruction of the computer, whereby the flooding phenomenon can be prevented.

Figure 5:
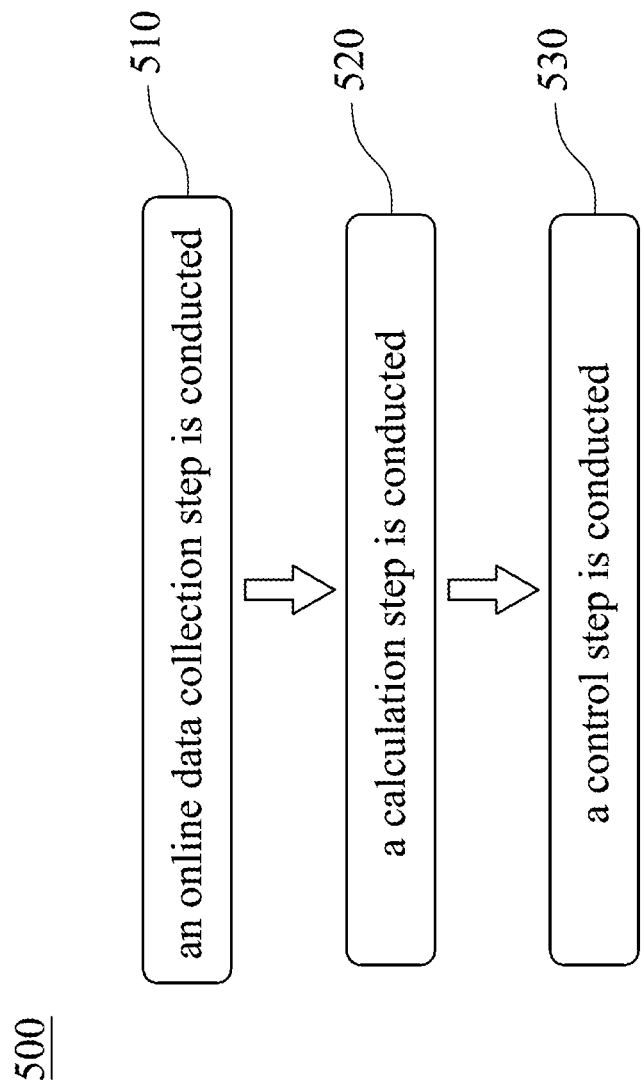
FIG. 5 is a flow diagram showing a method of real-time prognosis of a flooding phenomenon in a packed column according to yet another embodiment of the present disclosure.

FIG. 5 is a flow diagram showing a method of real-time prognosis of a flooding phenomenon in a packed column 500 according to yet another embodiment of the present disclosure. The method of real-time prognosis of the flooding phenomenon in the packed column 500 includes Step 510, Step 520 and Step 530.

In Step 510, an online data collection step is conducted. In Step 520, a calculation step is conducted, wherein the values of the pressure drop are used to calculate a value of a steadiness index. Details of Step 510 to Step 520 can be the same as that of Step 110 to Step 120 in FIG. 1, and are not repeated herein.

In Step 530, a control step is conducted, wherein the value of the steadiness index is compared to a control limit, and an alarm is triggered when the value of the steadiness index is greater than the control limit. Moreover, the value of the steadiness index and the control limit can be plotted in a control chart. Therefore, it is favorable to directly monitor the flooding phenomenon of the packed column in real time via a graphic presentation. Step 510 to Step 530 can be repeated for continuously monitoring the flooding phenomenon in the packed column.

In the embodiment, Step 530 can be implemented by a SPC method. In brief, according to the method of real-time prognosis of the flooding phenomenon in the packed column 500, a plurality of values of the steadiness index are collected in advance, and the plurality of values of the steadiness index are analyzed to determine a control limit in advance. Afterward, the pre-determined control limit is applied to monitor the values of the steadiness index which are calculated online when the packed column is under operation, so that the flooding phenomenon inside the packed column can be monitored in real time. In the embodiment, the control limit in Step 530 can be determined based on a nonparametric SPC method using kernel density estimation (Hereinafter, KDE SPC method), and can be directly compared to the value of the steadiness index calculated online. Both of the KDE and the MW-test are suitable for the cases where the variable distribution information is lacking (in the present disclosure, the variable is the steadiness index). However, the principle of the KDE is estimating the distribution by analyzing the data sample of the variable, and the principle of the MW-test is transferring the unknown distribution into a known distribution by Formula (8). That's why a value of the monitoring statistic calculated from Formula (8) is necessary for the MW-test, and a value of the monitoring statistic is unnecessary for the KDE. Specifically, the KDE can estimate the variable distribution by Formula (11):

$$\hat{f}_h(x) = \frac{1}{nh}\sum_{i=1}^{n}K\left(\frac{x-x_i}{h}\right); \quad (11)$$

wherein $\hat{f}$ is a probability density function (PDF), $x_i$ is a data point in a training sample set, x is an arbitrary data point drawn from the same statistical distribution, h is a bandwidth, K is a kernel function, i is an integral from 1 to n, and n is the number of the data points $x_i$ in the training sample set.

The following outlines how to determine the control limit with the KDE SPC method. First, the PDF calculated from Formula (11) is integrated so as to obtain a cumulative distribution function (CDF). After the ARLo is determined, the control limit can be obtained by CDF. For example, when ARLo=500 (which means the probability of a normal data point (i.e., a data point collected when the process is in control) greater than the control limit is 0.2%), the value of x which makes the value of CDF equal to 99.8% is the control limit. How to calculate the control limit corresponding to a different ARLo has been discussed in relevant literature and is not described herein.

Figure 6:
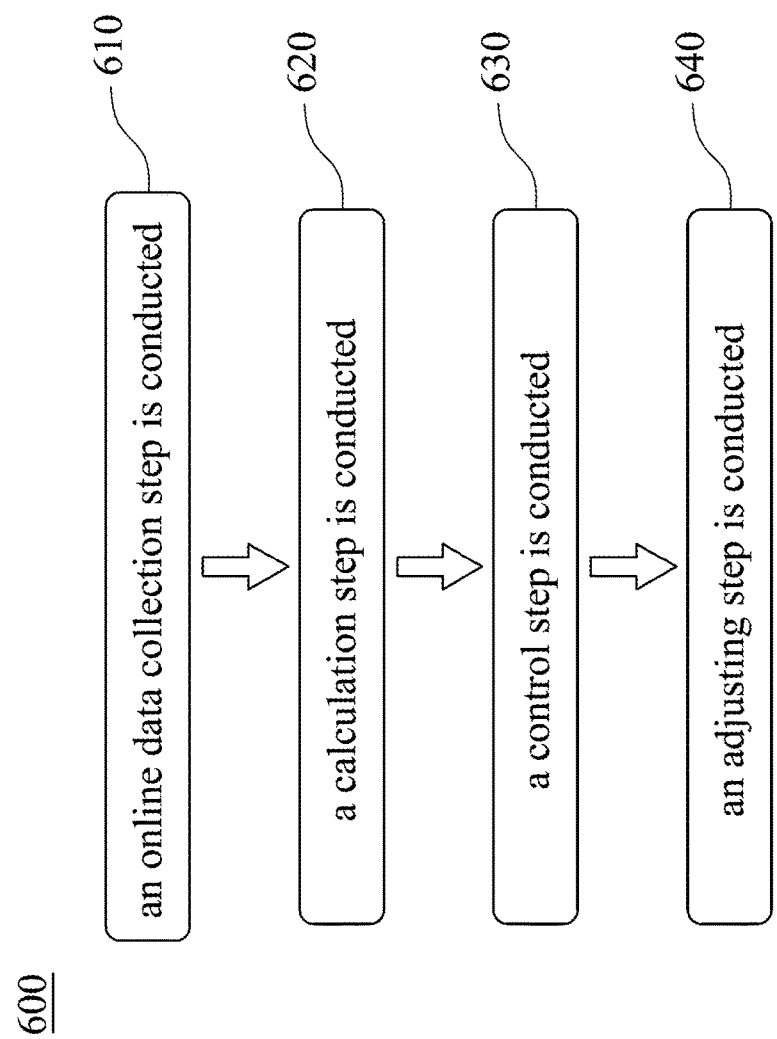
FIG. 6 is a flow diagram showing a method of real-time prognosis of a flooding phenomenon in a packed column according to further another embodiment of the present disclosure.

FIG. 6 is a flow diagram showing a method of real-time prognosis of a flooding phenomenon in a packed column 600 according to further another embodiment of the present disclosure. In FIG. 6, the method of real-time prognosis of the flooding phenomenon in the packed column 600 includes Step 610, Step 620, Step 630 and Step 640.

In Step 610, an online data collection step is conducted. In Step 620, a calculation step is conducted. In Step 630, a control step is conducted. Details of Step 610 to Step 630 can be the same as that of Step 510 to Step 530 in FIG. 5, and are not repeated herein.

In Step 640, an adjusted step is conducted. Details of Step 640 can be the same as that of Step 450 in FIG. 4, and are not repeated herein.

In the forgoing, the MW SPC method and the KDE SPC method are used to illustrate how to monitor the value of the steadiness index via the SPC methods, both of which are exemplary, thus the method according to the present disclosure is not limited thereto. As mentioned above, the steadiness index can extract useful process information from the pressure drop. Therefore, the SPC methods which can detect the shift of the values of the steadiness index and are irrelevant to the distribution of the sample data are all suitable for the present disclosure.

Examples

Figure 7:
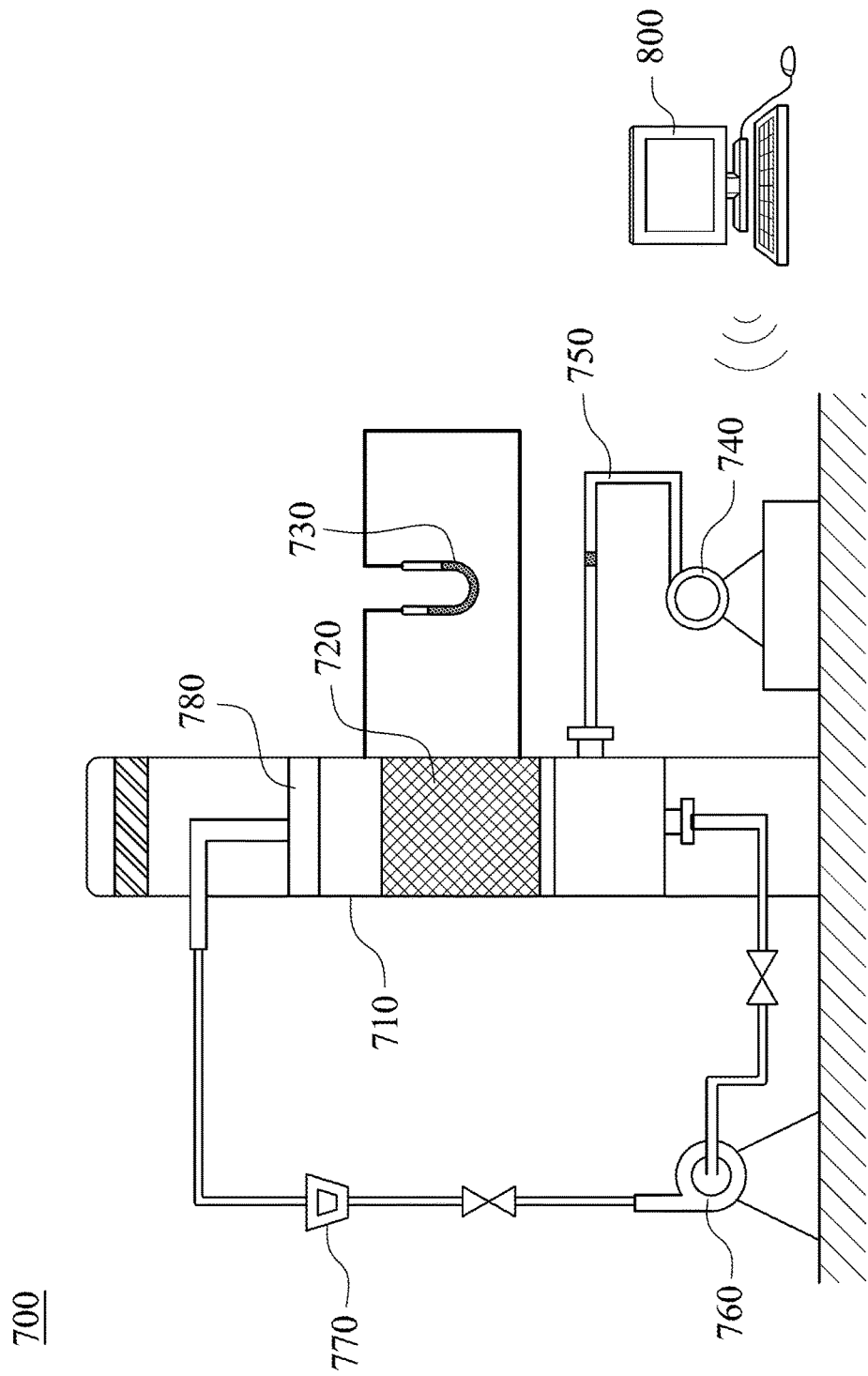
FIG. 7 is a schematic view of a packed column used in examples according to the present disclosure.

FIG. 7 is a schematic view of a packed column 700 used in the examples according to the present disclosure. Experiments are conducted with the packed column 700 to observe if the method according to the present disclosure can accurately predict the flooding phenomenon. The packed column 700 includes a column body 710, a packing layer 720, a sensing and transmitting element 730, a blower 740, an air inlet pipe 750, a liquid pump 760, a flowmeter 770 and a liquid distributor 780. The wall of the column body 710 is made of transparent glass, so that the flooding phenomenon can be directly observed by human eyes. When the packed column 700 is under operation, the gas (not shown) enters into the lower portion of the column body 710 from the air inlet pipe 750, then enters upwardly into the packing layer 720; the liquid (not shown) is pumped into the upper portion of the column body 710 by the liquid pump 760, and enters downwardly into the packing layer 720 after being distributed evenly by the liquid distributor 780. The sensing and transmitting element 730 is a differential pressure transmitter (EJA120, Yokogawa). The sensing and transmitting element 730, the blower 740 and the liquid pump 760 are connected with the computer 800 (via a wired or wireless connection). The values of the pressure drop measured by the sensing and transmitting element 730 can be delivered to the computer 800 by the sensing and transmitting element 730 in real time, and the values of the pressure drop are recorded by the computer 800. The blower 740 and the liquid pump 760 can change the operational condition of the packed column 700 according to an instruction of the computer 800. For example, the blower 740 can change the gas flow rate, and the liquid pump 760 can change the liquid flow rate. More specifically, the values of the pressure drop are measured and transferred into current signals of 4-20 mA by the sensing and transmitting element 730, and then be delivered through the wire to the input/output signal card (not shown) installed in the computer 800 based on the RS-485 communication, so that the values of the pressure drop can be recorded by the computer 800. Moreover, the instruction of the computer 800 can be delivered to the blower 740 and the liquid pump 760 through the wire so as to adjust the gas flow rate or the liquid flow rate. According to the present disclosure, the gas is air, and the liquid is water. Moreover, the experiments are conducted under normal temperature and pressure.

Example 1 a preflooding step is conducted before the formal experiment, i.e., let the flooding phenomenon occur in the packed column 700 and maintain for a period of time, so that the packings of the packing layer 720 can be soaked thoroughly, and the inaccuracy resulted from the incomplete soaking can be prevented. Afterward, the experiment is formally conducted. During the experiment, the liquid flow rate is approximately fixed at $1.15 \times 10^{-4}$ m$^3$/s, the gas flow rate is increased stepwise, and each gas flow rate is maintained for 10 minutes. The values of the pressure drop are measured by the sensing and transmitting element 730 with a frequency of 1200 times per minutes and are recorded by the computer 800. The experiment is conducted until the flooding phenomenon is observed by human eyes.

Example 2 the liquid flow rate is approximately fixed at $1.45 \times 10^4$ m$^3$/s, and other experimental conditions are the same as that of Example 1.

Example 3 the liquid flow rate is approximately fixed at $0.89 \times 10^4$ m$^3$/s, the gas flow rate is increased continuously at a rate of 0.1 m$^3$/h (i.e., $2.78 \times 10^{-5}$ m$^3$/s) per second, and other experimental conditions are the same as that of Example 1.

Figure 8:
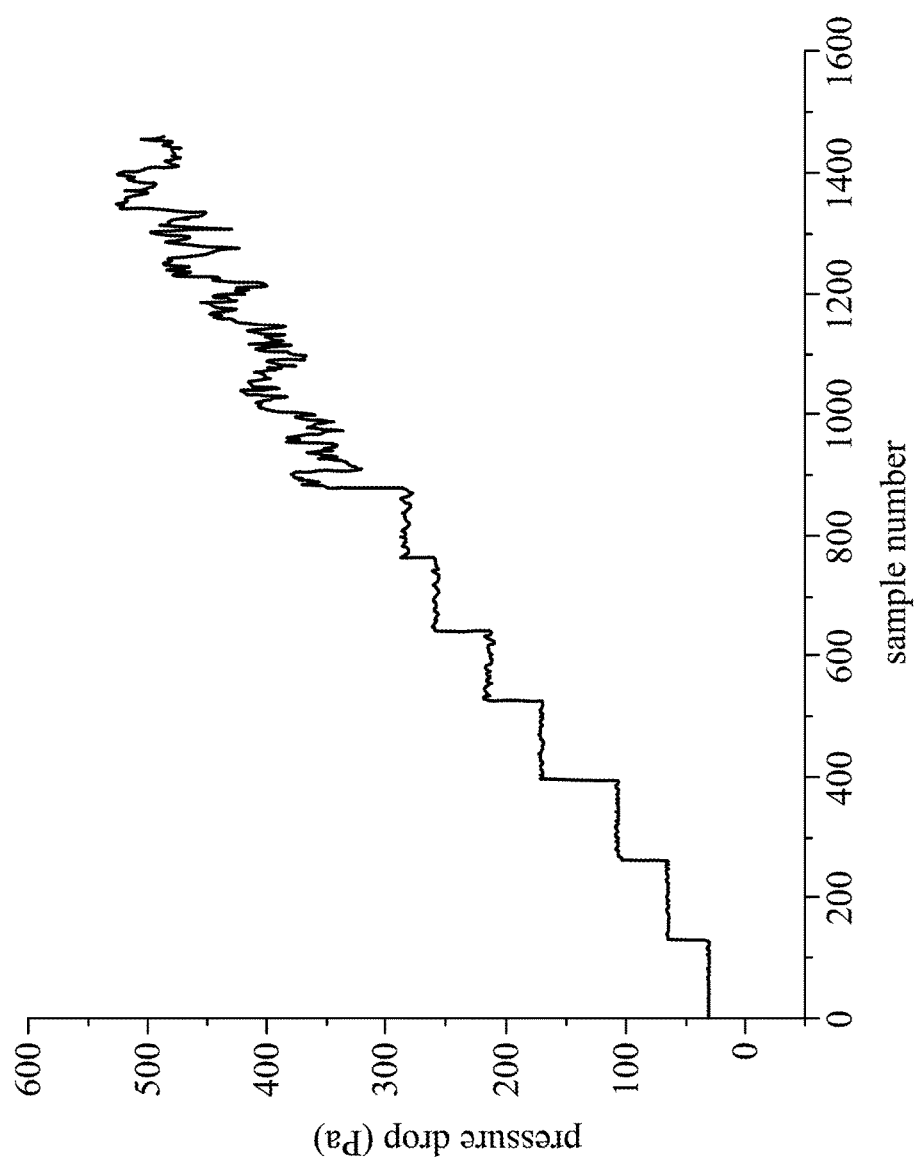
FIG. 8 is a diagram showing a trajectory of pressure drop in Example 1.
Figure 9:
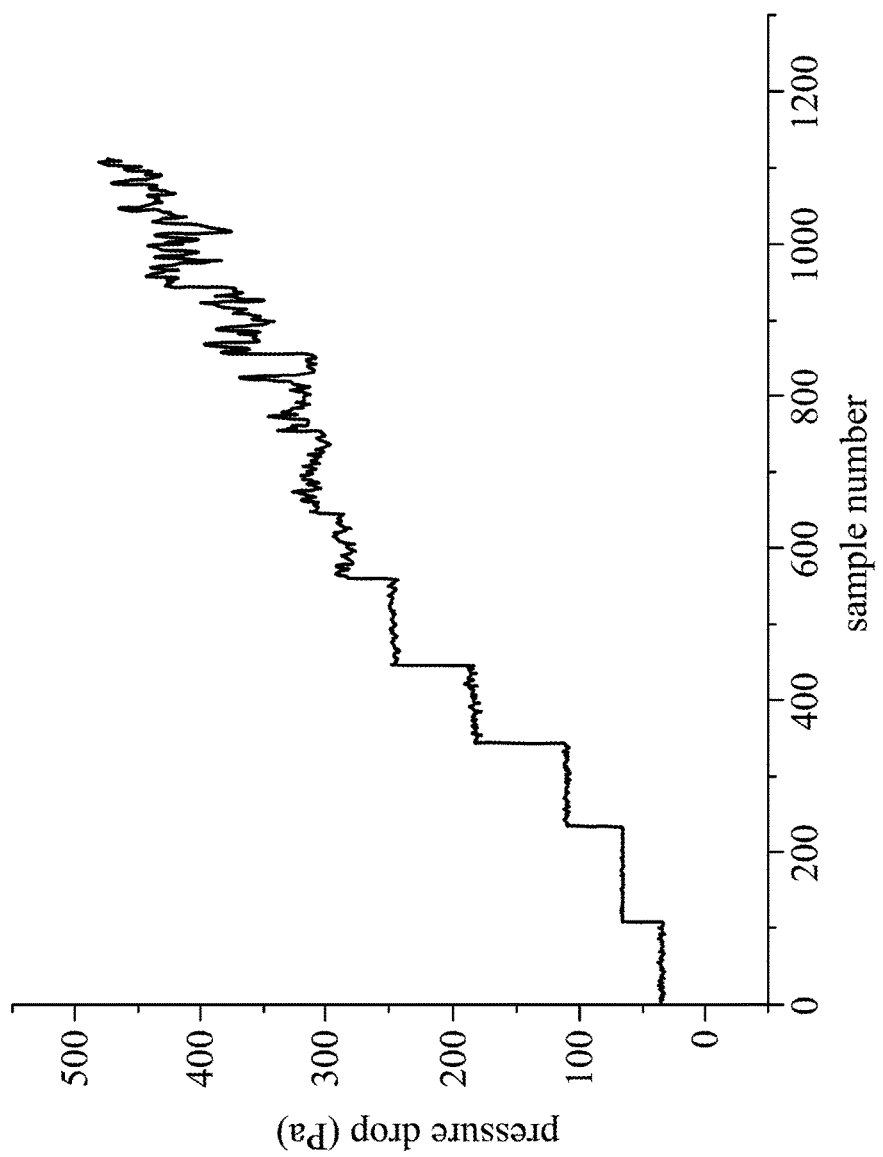
FIG. 9 is a diagram showing a trajectory of pressure drop in Example 2.
Figure 10:
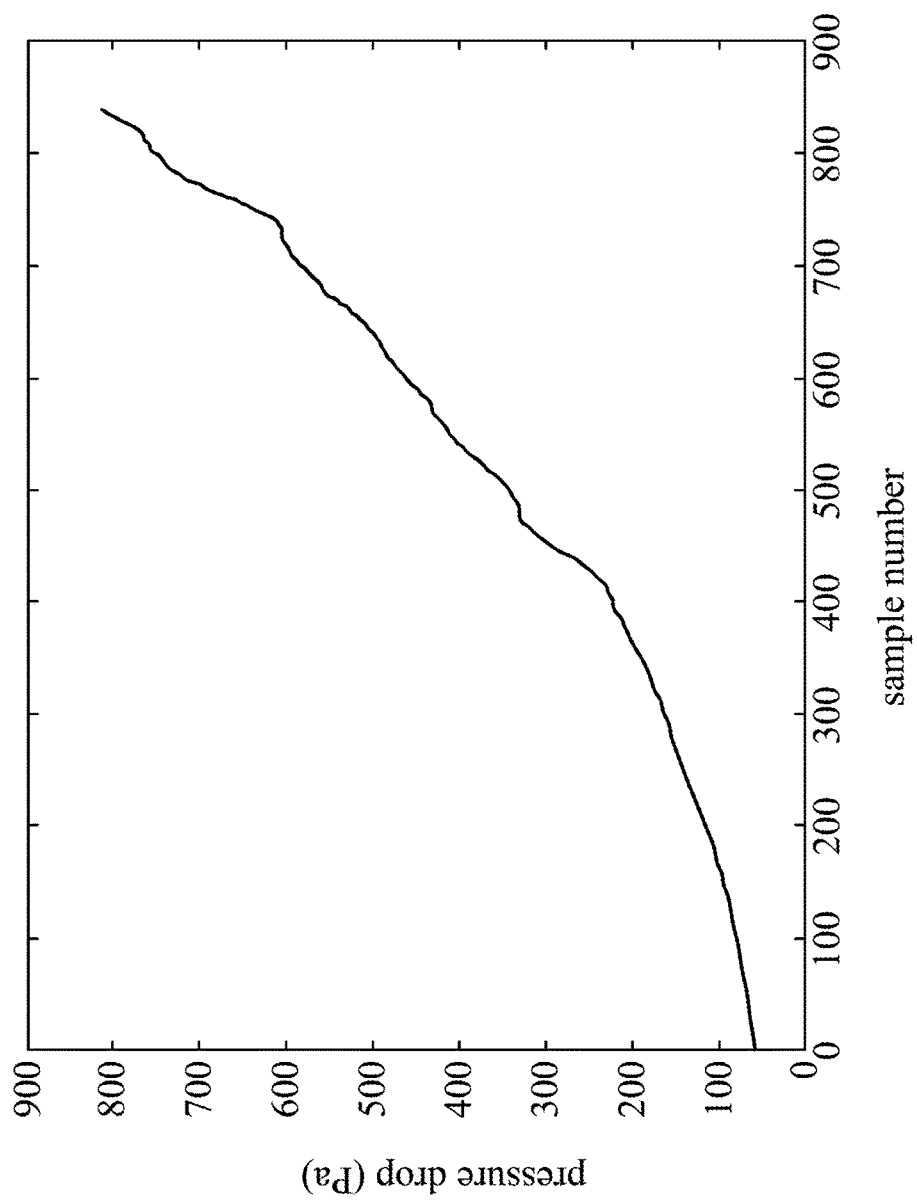
FIG. 10 is a diagram showing a trajectory of pressure drop in Example 3.

FIG. 8 is a diagram showing a trajectory of pressure drop in Example 1. FIG. 9 is a diagram showing a trajectory of pressure drop in Example 2. FIG. 10 is a diagram showing a trajectory of pressure drop in Example 3. In FIGS. 8-10, the vertical axis represents the pressure drop, and unit thereof is Pa; the horizontal axis represents the sample number (also called sampling interval). Table 2 shows the relationship between the wind frequency and the sample number in Example 1. Table 3 shows the relationship between the wind frequency and the sample number in Example 2. In Table 2 and Table 3, "*" represents the flooding period (i.e., the flooding phenomenon is happening). The wind frequency is an adjusting parameter of the blower 740. Different gas flow rates can be obtained by adjusting the wind frequency of the blower 740.

TABLE 2

| | wind frequency (kHz) | | | |
| --- | --- | --- | --- | --- |
| | 10 | 15 | 20 | 25 |
| sample number | 1~129 | 130~263 | 264~396 | 397~526 |
| | wind frequency (kHz) | | | |
| | 27 | 29 | 30 | 31 |
| sample number | 527~640 | 641~763 | 764~878 | 879~1004 |
| | wind frequency (kHz) | | | |
| | 32* | 33* | 34* | 35* |
| sample number | 1005~1127 | 1128~1264 | 1265~1387 | 1388~1460 |

TABLE 3

| | wind frequency (kHz) | | | |
| --- | --- | --- | --- | --- |
| | 10 | 15 | 20 | 25 |
| sample number | 1~108 | 109~233 | 234~342 | 343~445 |
| | wind frequency (kHz) | | | |
| | 28 | 30 | 31 | 32* |
| sample number | 446~559 | 560~644 | 645~753 | 754~855 |
| | wind frequency (kHz) | | | |
| | 33* | 34* | 35* | |
| sample number | 856~943 | 944~1043 | 1044~1113 | |

As shown in FIGS. 8-10 and Tables 2-3, the sample mean and the sample variance of the values of the pressure drop are affected by the change of the gas flow rate and the change of the liquid low rate. In FIGS. 8-9, the trajectory of pressure drop is ladder-shaped, so that FIG. 10 is closer to the practical operation of the packed column 700 (i.e., the gas flow rate increases continuously) than FIGS. 8-9. In FIG. 10, the sample mean and the sample variance of the values of the pressure drop are affected by the change of gas flow rate, so that the slope of the trajectory is incremental. Therefore, the operation of the packed column 700 violates the basic assumption of the conventional SPC method. Accordingly, the conventional SPC method does not applicable to establish the control limit and the control chart for the values of the pressure drop. However, in the method according to the present disclosure, the pressure drop are transformed into the steadiness index, which allows the SPC method applicable to predict the flooding phenomenon in the packed column 700 in real time.

Figure 11:
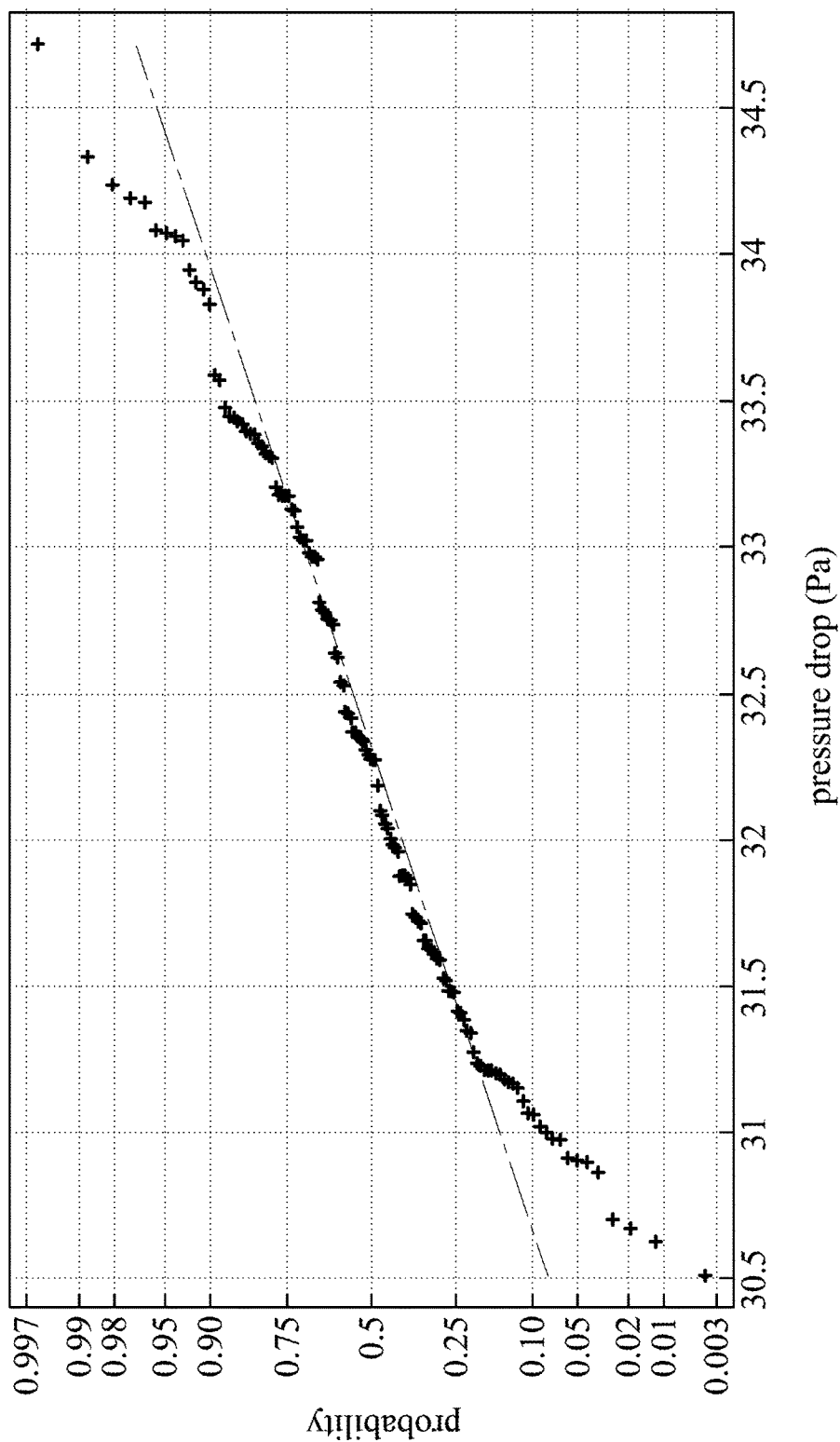
FIG. 11 is a normal probability plot of a part of values of the pressure drop in Example 1.
Figure 12:
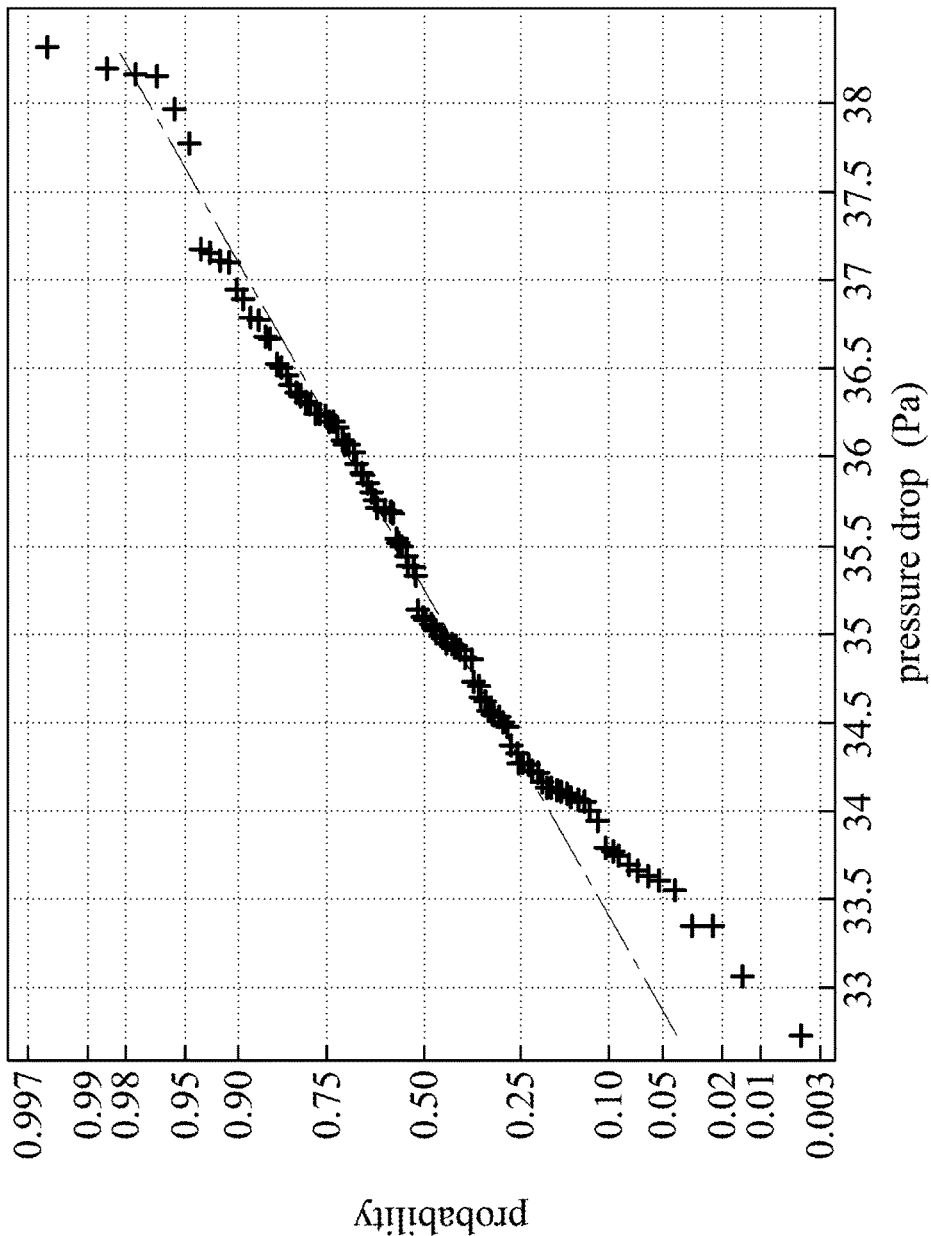
FIG. 12 is a normal probability plot of a part of values of the pressure drop in Example 2.

FIG. 11 is a normal probability plot of a part of values of the pressure drop in Example 1. FIG. 12 is a normal probability plot of a part of values of the pressure drop in Example 2. The part of values of the pressure drop in FIG. 11 is obtained from the first stair in FIG. 8, and the part of values of the pressure drop in FIG. 12 is obtained from the first stair in FIG. 9. FIGS. 11-12 show that even the gas flow rate and the liquid flow rate are fixed, the distributions of the values of the pressure drop in Example 1 and Example 2 are not Gaussian distributions.

Figure 13:
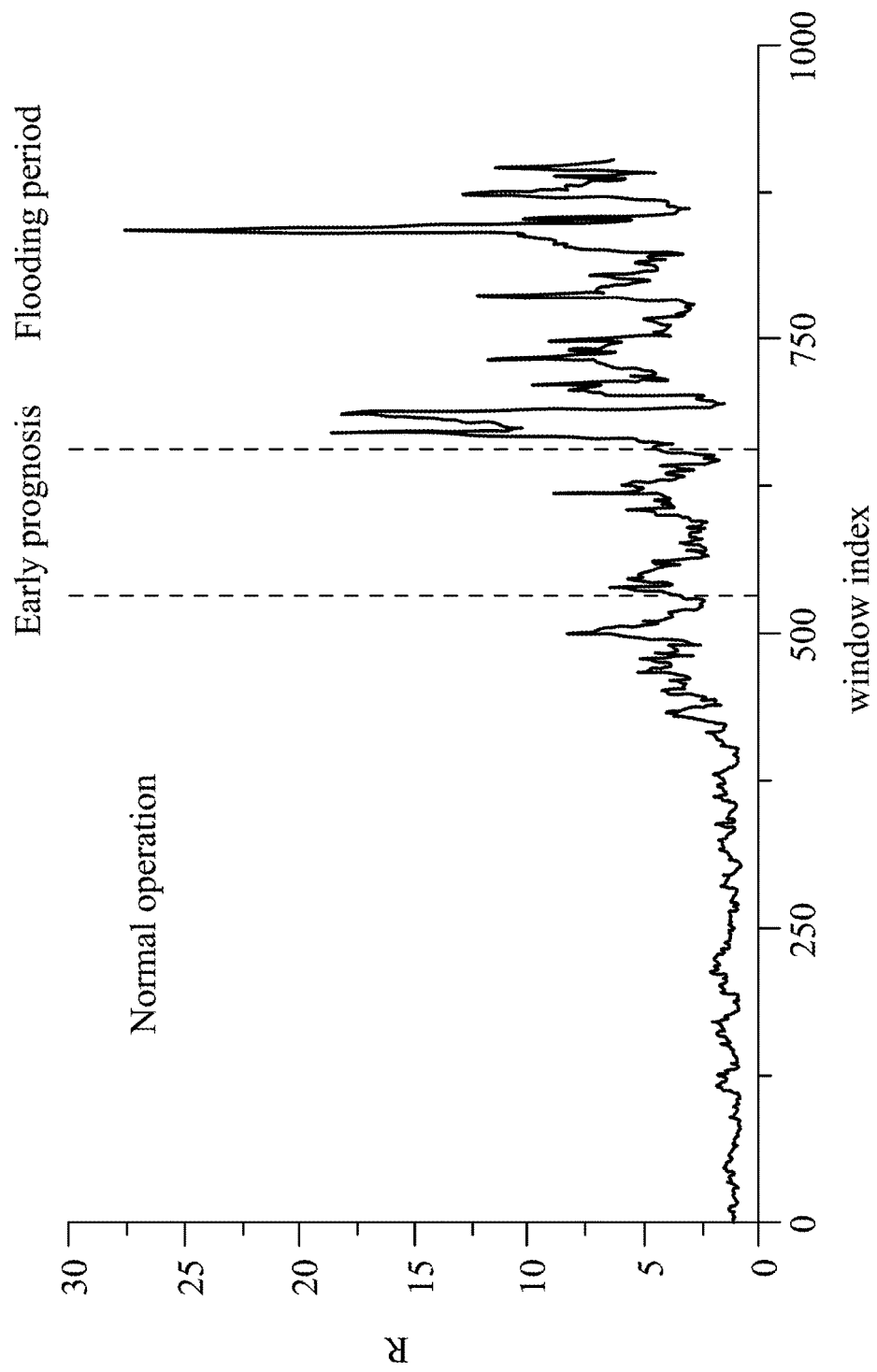
FIG. 13 is a diagram showing a trajectory of R in Example 1.
Figure 14:
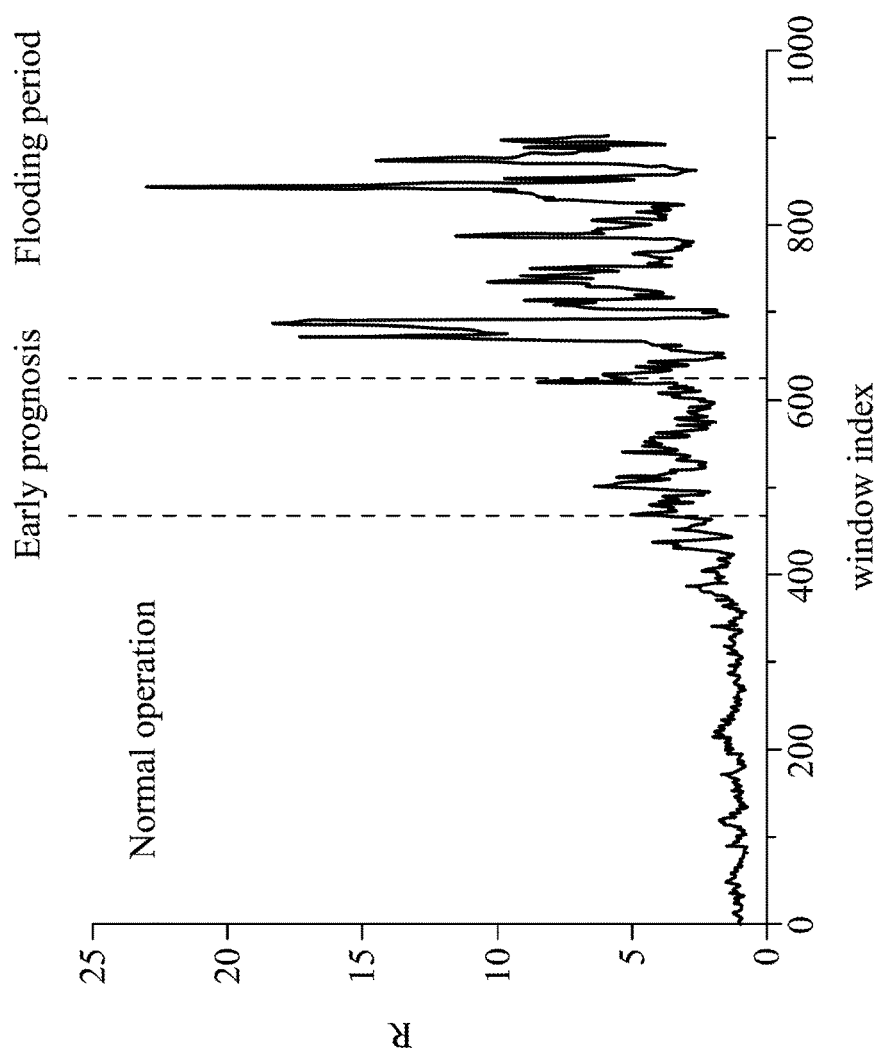
FIG. 14 is a diagram showing a trajectory of R in Example 2.
Figure 15:
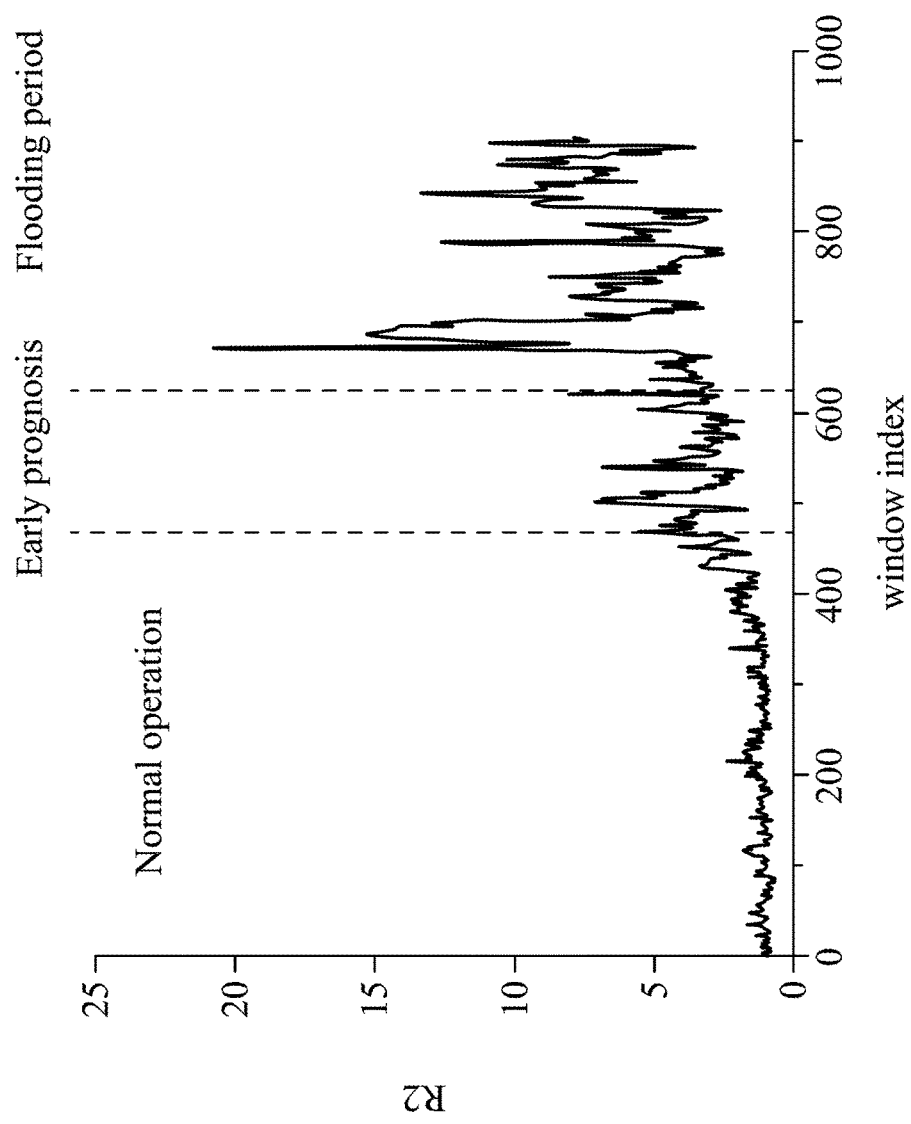
FIG. 15 is a diagram showing a trajectory of R2 in Example 2.

The values of the pressure drop in Example 1 and Example 2 are used to calculate a plurality of values of the steadiness index R (with Formulas (1)-(3)) by the method of moving the time widow online, wherein the size of the time window is 20, and the step length of the time window is 1 (i.e., there are 20 values of the pressure drop in each time window, and the interval between the current time window and the next time window is 1 value of the pressure drop). Each of the values of the steadiness index R and the corresponding window index thereof are plotted to obtain a trajectory of R. Moreover, the values of the pressure drop of Example 2 are calculated to obtain a plurality of values of the steadiness index R2 (with Formulas (4)-(7)) by the method of moving the time widow online, wherein the size of the time window is 20, and the step length of the time window is 1. Each of the values of the steadiness index R2 and the corresponding window index thereof are plotted to obtain a trajectory of R2. FIG. 13 is a diagram showing the trajectory of R in Example 1. FIG. 14 is a diagram showing the trajectory of R in Example 2. FIG. 15 is a diagram showing the trajectory of R2 in Example 2. In each of FIGS. 13-15, three stages are divided by the dash line. The first stage is named as "normal operation", wherein the packed column 700 is under normal operation. The second stage is named as "early prognosis", wherein the flooding phenomenon is about to happen or the flooding phenomenon is slight. The third stage is named as "flooding period", wherein the flooding phenomenon is obvious. The three stages are divided according to the phenomena observed by the eyes of the process engineer.

Figure 16:
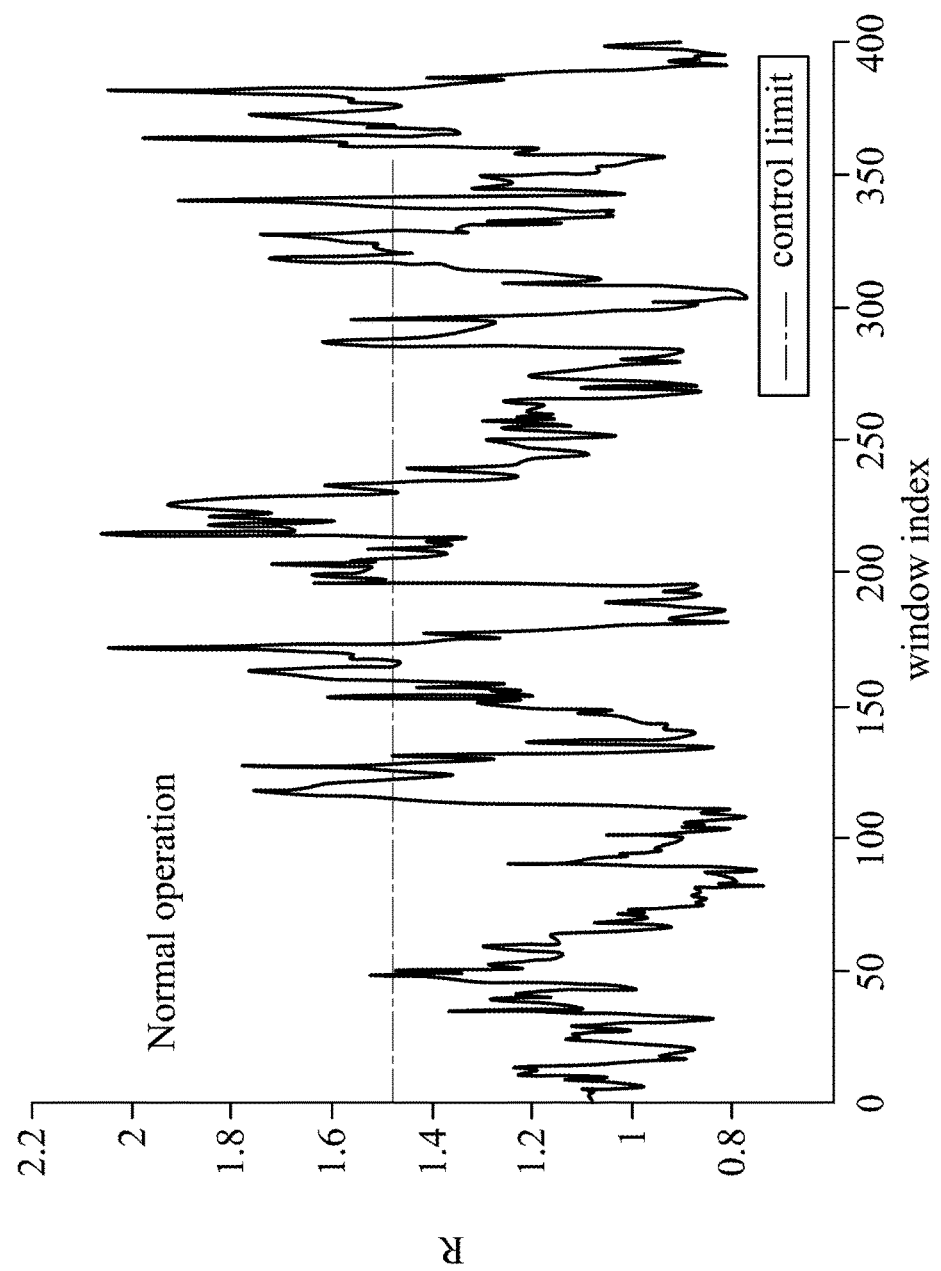
FIG. 16 is a control chart for R in Example 1.

If the distribution of the values of the steadiness index R is a Gaussian distribution, the control limit thereof is 1.47965, which is obtained by looking up a conventional statistical distribution table. FIG. 16 is a control chart for R in Example 1, in which the control limit 1.47965 is added therein. As shown in FIG. 16, the value of the steadiness index R may be greater than the control limit even in the stage of normal operation and trigger a false alarm, which shows the distribution of the values of the steadiness index R is not a Gaussian distribution. That is, the control limit of R cannot be obtained by looking up the conventional statistical distribution table.

Then, the control chart is plotted based on the MW SPC method, in which the monitoring statistic is calculated based on the values of the steadiness index R. First, a training sample set and a control limit are provided. The training sample set are the values of the steadiness index R calculated from the values of the pressure drop in control (corresponding to $R_{Yi}$ in Formula (8)). The control limit can be obtained as follows. The values of ARLo, m1, m2 are first determined, which are: ARLo=500; m1=500; and m2=5. Thus, the control limit is 2172, which is obtained by looking up Table 1.

Figure 17:
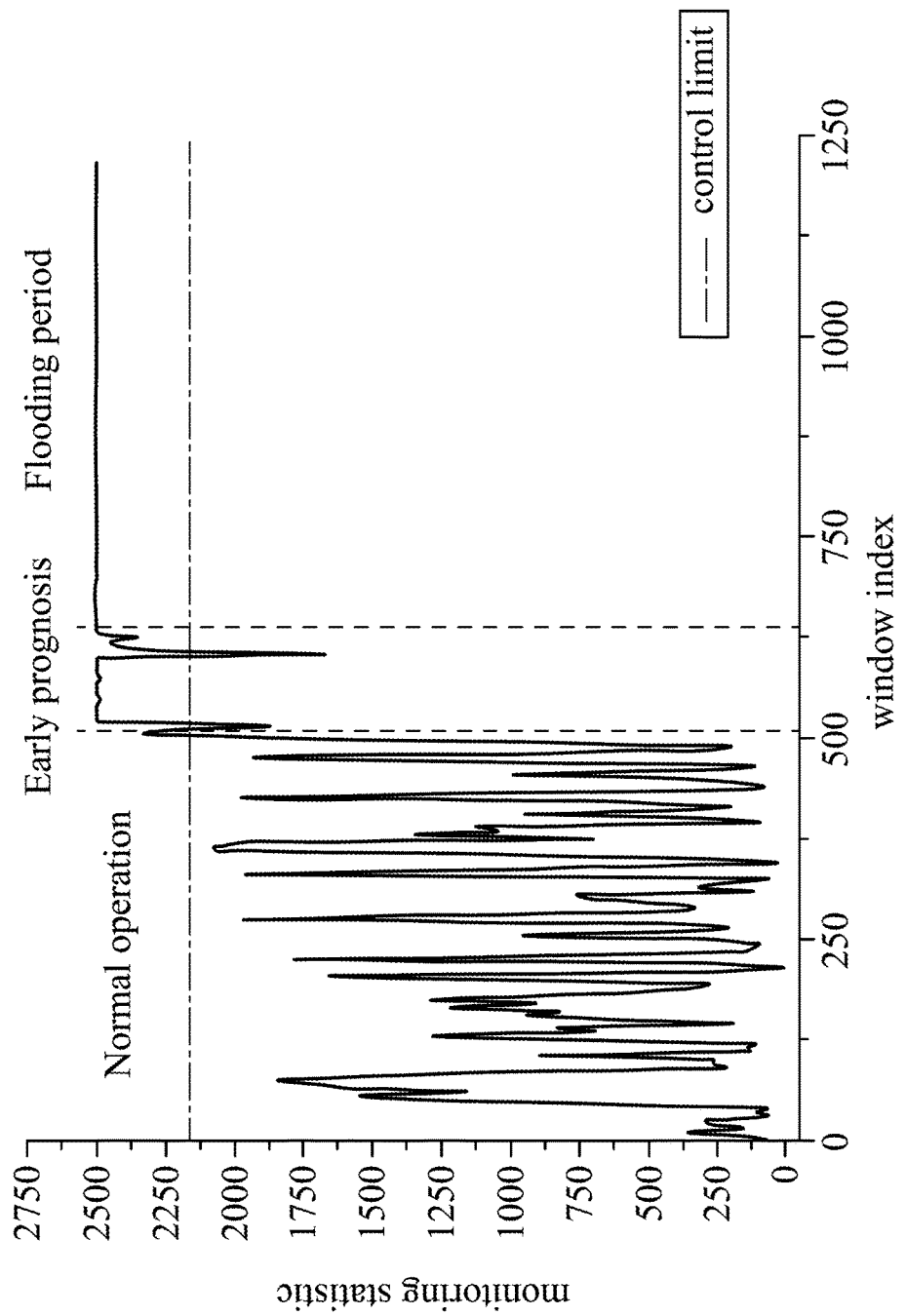
FIG. 17 is a control chart based on a nonparametric SPC method using Mann-Whitney test in Example 1.
Figure 18:
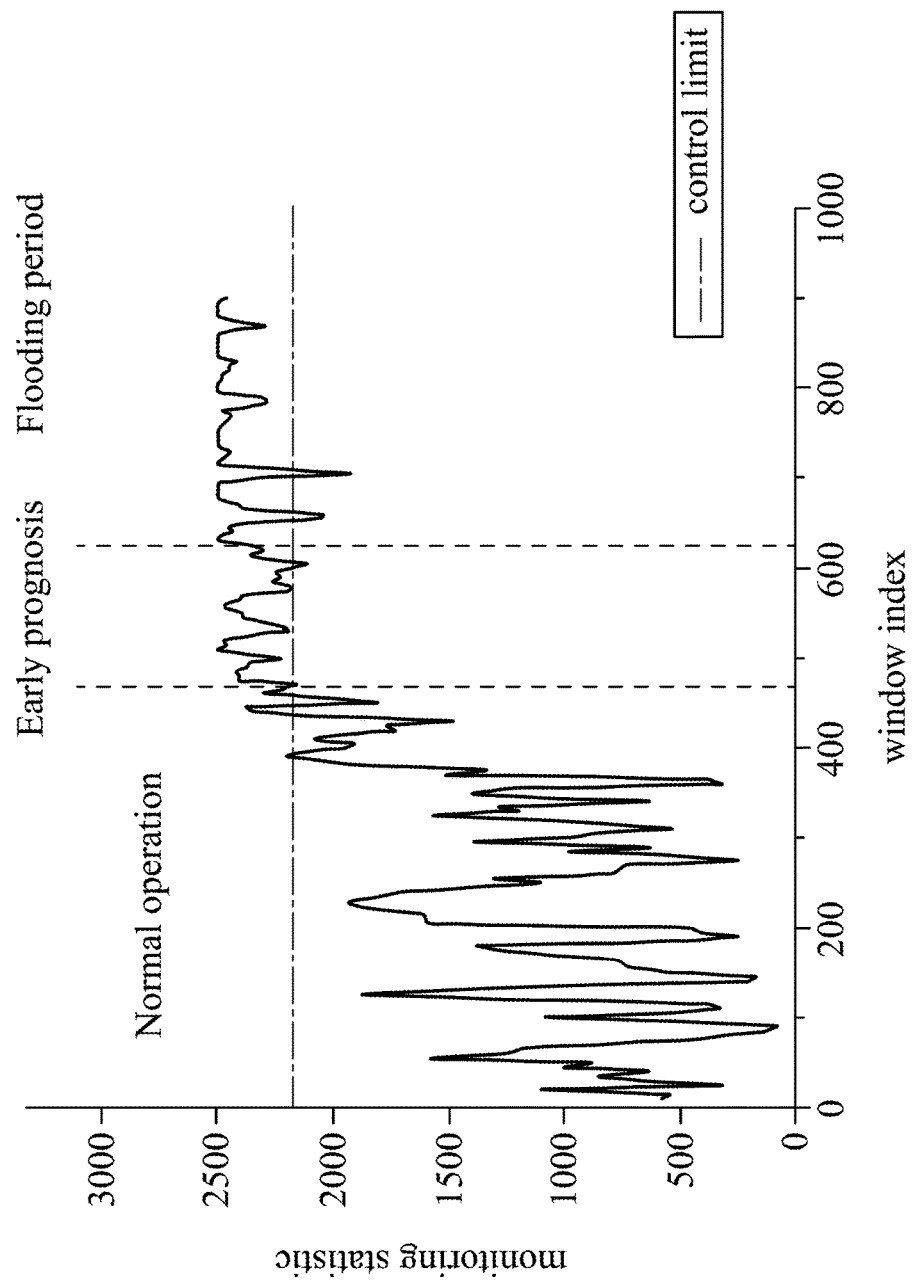
FIG. 18 is a control chart based on a nonparametric SPC method using Mann-Whitney test in Example 2.

Afterward, the monitoring statistic is calculated according to Formula (8) based on the values of the steadiness index R calculated online (corresponding to $R_{Yj}^{h}$ in Formula (8)) in Example 1. In Formula (8), the test sample set of the values of the steadiness index R can be selected by the method of moving the time widow online, the size of the time window is defined as 5 (which equals to the size of the test sample set m2), and the step length of the time window is defined as 1. Then the value of the monitoring statistic in each time window is calculated accordingly (the window index equals to h in Formula (8)). The control limit and the value of the monitoring statistic in each time window are plotted in the control chart. FIG. 17 is the control chart based on an MW SPC method in Example 1, in which the vertical axis represents the monitoring statistic calculated from the values of the steadiness index R (obtained by Formulas (1)-(3)), and the horizontal axis represents the window index (the number of the time window). As shown in FIG. 17, when the packed column 700 is under normal operation, almost all the values of the monitoring statistic are lower than the control limit. When the flooding phenomenon is about to happen or when the flooding phenomenon is slight (corresponding to the stage of early prognosis in FIG. 17), or when the flooding phenomenon is obvious (corresponding to the stage of flooding period in FIG. 17), the values of the monitoring statistic are almost all higher than the control limit. In other words, when the method according to the present disclosure is applied to monitor the flooding phenomenon in the packed column 700, an alarm is triggered when the value of the monitoring statistic is greater than the control limit which represents the flooding phenomenon is going to happen. Accordingly, the operational conditions of the packed column 700 can be adjusted in time, and the flooding phenomenon can be prevented effectively. The control limit and the training sample set obtained in Example 1 are directly apply to Example 2, and the values of the steadiness index R calculated online (corresponding to $R_{Yj}^h$ in Formula (8)) in Example 2 are treated as the test sample set and are used to obtain the value of the monitoring statistic by using Formula (8). The calculation method adopted in Example 2 is the same as that in Example 1. Then the control limit and the values of the monitoring statistic in different time windows are plotted in a control chart. FIG. 18 is the control chart based on the MW SPC method in Example 2, in which the vertical axis represents the monitoring statistic calculated from the values of the steadiness index R (obtained by Formulas (1)-(3)), and the horizontal axis represents the window index.

Figure 19:
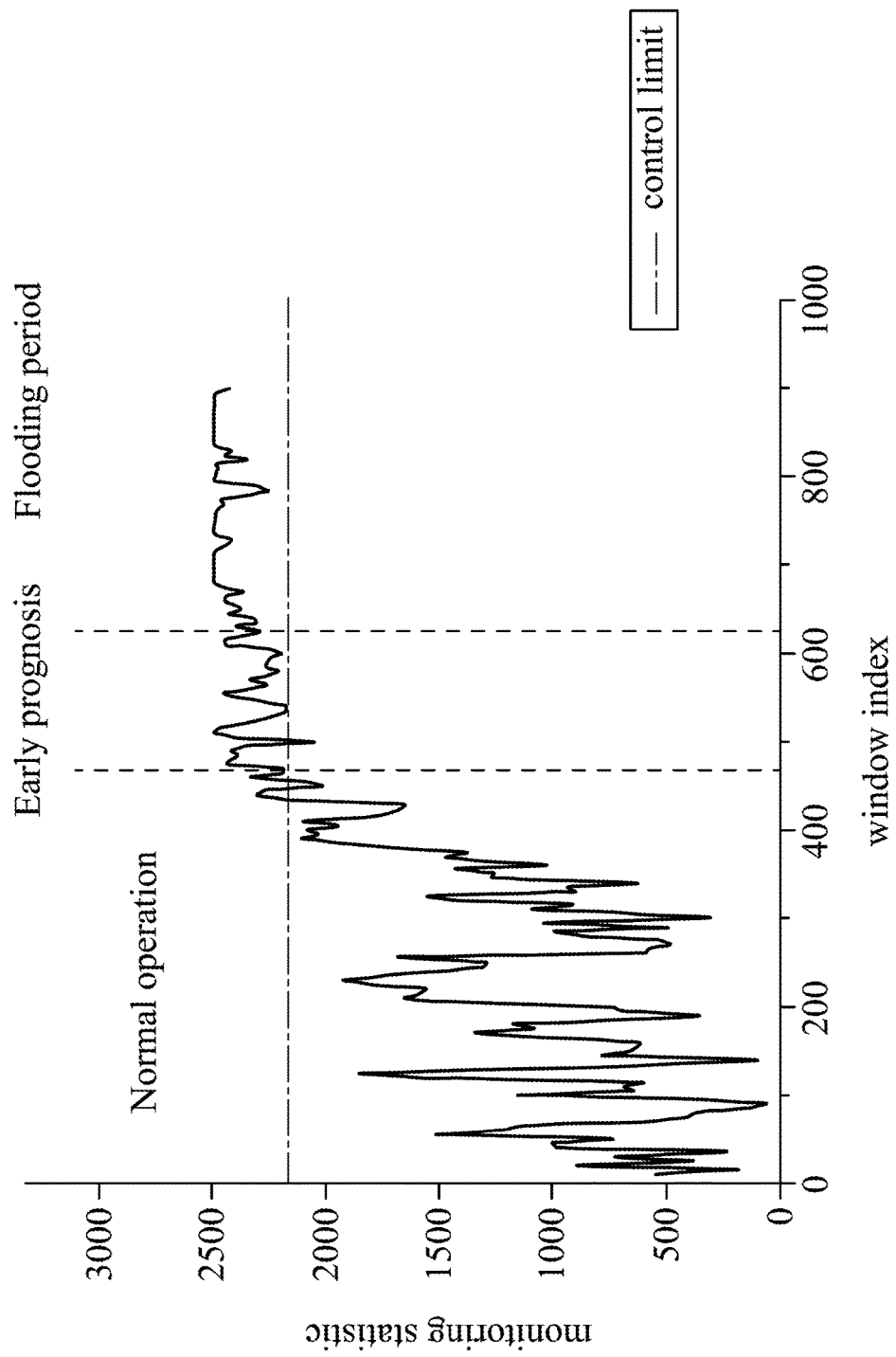
FIG. 19 is another control chart based on a nonparametric SPC method using Mann-Whitney test in Example 2.

The control limit and the training sample set obtained in Example 1 are directly apply to Example 2, and the values of the steadiness index R2 calculated online (corresponding to $R_{Yj}^h$ in Formula (8)) in Example 2 are treated as the test sample set and are used to obtain the value of the monitoring statistic by using Formula (8). The calculation method adopted in Example 2 is the same as that in Example 1. Then the control limit and the value of the monitoring statistic in each time window are plotted in a control chart. FIG. 19 is another control chart of the MW SPC method in Example 2, in which the vertical axis represents the monitoring statistic calculated from the values of the steadiness index R2 (obtained by Formulas (4)-(7)), and the horizontal axis represents the window index.

As shown in FIGS. 18 and 19, when the packed column 700 is under normal operation, almost all the values of the monitoring statistic are lower than the control limit. When the flooding phenomenon is about to happen or when the flooding phenomenon is slight (corresponding to the stages of early prognosis in FIG. 18 and FIG. 19), or when the flooding phenomenon is obvious (corresponding to the stages of flooding period in FIG. 18 and FIG. 19), the values of the monitoring statistic are almost all higher than the control limit. It is clear that the method according to the present disclosure can trigger an alarm when the flooding phenomenon is still slight (i.e., in the stage of early prognosis), and the operational conditions of the packed column 700 can be adjusted in time. Accordingly, the flooding phenomenon can be effectively prevented.

Figure 20:
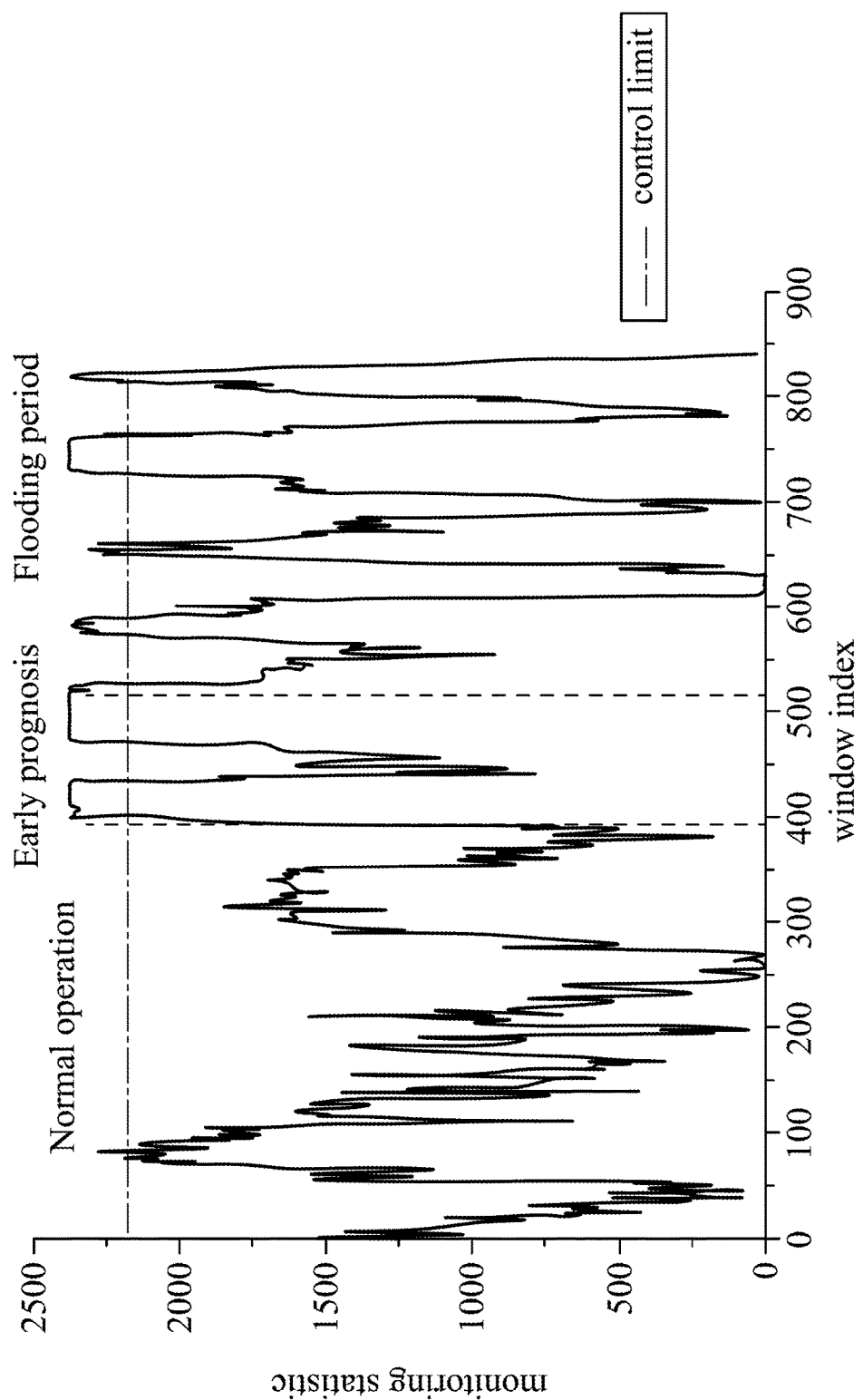
FIG. 20 is a control chart based on a nonparametric SPC method using Mann-Whitney test in Example 3.

The control limit and the training sample set obtained in Example 1 are directly apply to Example 3, and the values of the steadiness index R calculated online (corresponding to $R_{Yj}^h$ in Formula (8)) in Example 3 are treated as the test sample set and are used to obtain the value of the monitoring statistic by using Formula (8). The calculation method adopted in Example 3 is the same as that in Example 1. Then the control limit and the value of the monitoring statistic in each time window are plotted in a control chart. FIG. 20 is the control chart based on the MW SPC method in Example 3, in which the vertical axis represents the monitoring statistic calculated from the values of the steadiness index R (obtained by Formulas (1)-(3)), and the horizontal axis represents the window index. As shown in FIG. 20, only a false alarm occurred in the stage of normal operation, and when the flooding phenomenon is slight or obvious, the values of the monitoring statistic are almost all higher than the control limit. It is clear that the method according to the present disclosure can trigger an alarm when the flooding phenomenon is still slight (i.e., in the stage of early prognosis), and the operational conditions of the packed column 700 can be adjusted in time. Accordingly, the flooding phenomenon can be effectively prevented. Moreover, in FIGS. 18-20, the control limit and the training sample set used in Example 1 are directly apply to Examples 2-3. That is, it is unnecessary to determine the control limit and collect the training sample set each time to use the method according to the present disclosure to predict the flooding phenomenon in packed columns, which is extremely convenient.

Figure 21:
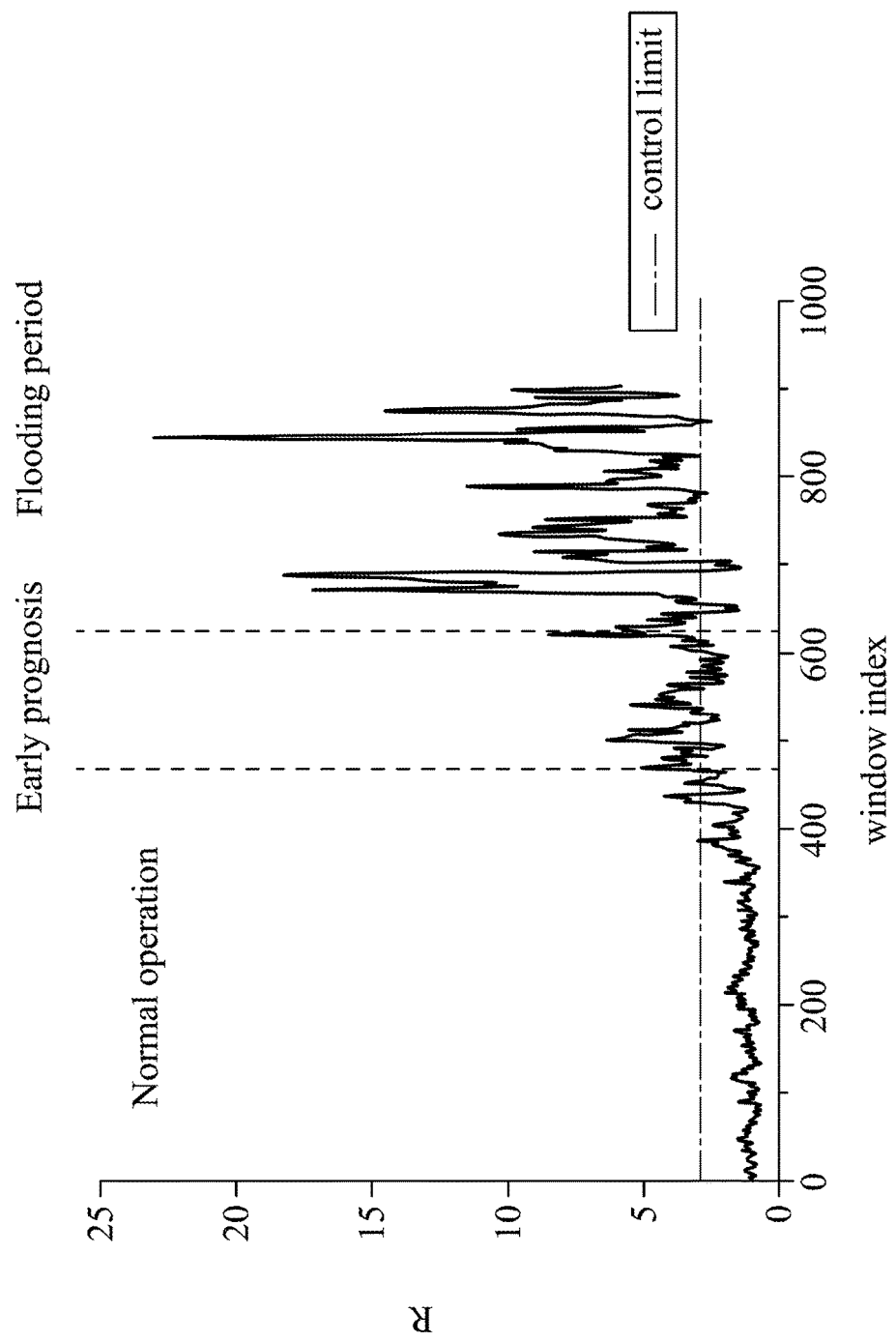
FIG. 21 is a control chart based on a nonparametric SPC method using kernel density estimation in Example 2.
Figure 22:
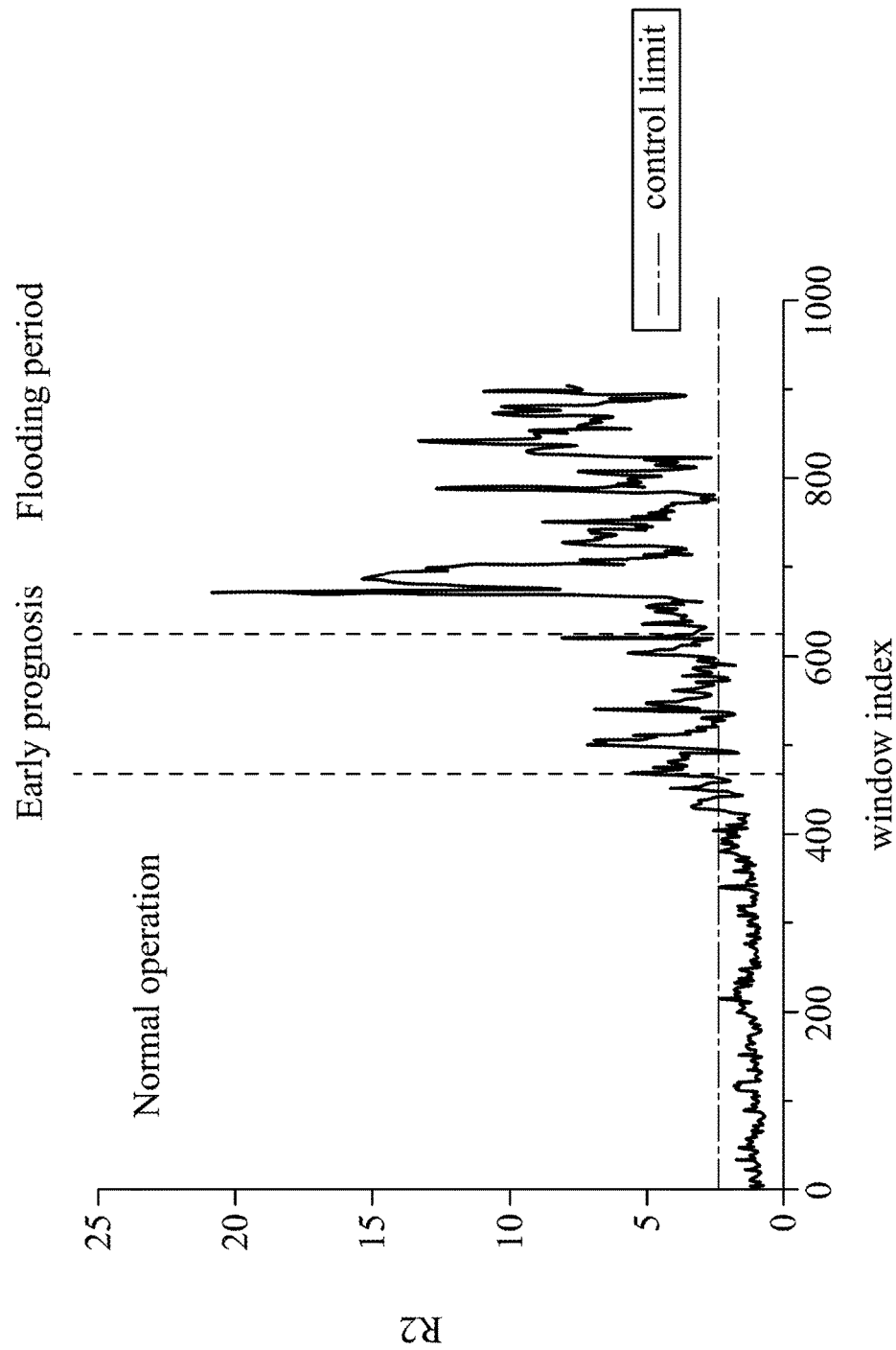
FIG. 22 is another control chart based on a nonparametric SPC method using kernel density estimation in Example 2.

Moreover, the values of the steadiness index R of Examples 1-3 can also be used to establish control charts based on the KDE SPC method. The following exemplarily illustrates how to obtain the control chart for Example 2 based on the KDE SPC method. FIG. 21 is the control chart based on the KDE SPC method in Example 2, in which the vertical axis represents R, and the horizontal axis represents the window index. The control limit in FIG. 21 is 2.914559, which is obtained with ARLo=500. Both of the values of the steadiness index R and the control limit are plotted in the control chart. FIG. 22 is another control chart based on the KDE SPC method in Example 2, in which the vertical axis represents R2, and the horizontal axis represents the window index. The control limit in FIG. 22 is 2.388284, which is obtained with ARLo=500. Both the values of the steadiness index R2 and the control limit are plotted in the control chart. As shown in FIGS. 21 and 22, when the packed column 700 is under normal operation, the values of the steadiness index (R and R2) are almost all lower than the control limit. When the flooding phenomenon in the packed column 700 is slight (corresponding to the stages of early prognosis in FIGS. 21 and 22) or obvious (corresponding to the stages of flooding period in FIGS. 21 and 22), the values of the steadiness index are almost all higher than the control limit. It is clear that the method according to the present disclosure can trigger an alarm when the flooding phenomenon is still slight (i.e., in the stage of early prognosis), and the operational conditions of the packed column 700 can be adjusted in time. Accordingly, the flooding phenomenon can be effectively prevented.

It should be stated that the examples of the present disclosure (Examples 1-3) are applied to prove that the method according to the present disclosure can predict slight flooding phenomenon and obvious flooding phenomenon. Therefore, in Examples 1-3, the gas flow rate is increased until the obvious flooding phenomenon happens, and the phenomena observed by the eyes of engineer (i.e., the stages of "Normal operation", "Early prognosis" and "Flooding period" labelled in FIGS. 13-22) are compared to the control limit and the values of the monitoring statistic/steadiness index obtained by the method according to the present disclosure for assessing if the method according to the present disclosure can effectively predict the slight and the obvious flooding phenomenon. In other words, the examples of the present disclosure (Examples 1-3) are not the test results of the method according to the present disclosure, but the verification results of the effectivity of the method according to the present disclosure. In practice, when the method according to the present disclosure is applied to predict the flooding phenomenon in packed columns in real time, an alarm is triggered when the value of the monitoring statistic/steadiness index is greater than the control limit, and the gas flow rate or liquid flow rate can be adjusted in time to prevent the flooding phenomenon. Therefore, the alarm is triggered before the early prognosis, which can prevent the flooding phenomenon effectively.

To sum up, in the present disclosure, the pressure drop are transformed into the steadiness index, and the steadiness index can be further transformed into the monitoring statistic or can be directly monitored, which enables the SPC method to be applied to the real-time prognosis of the flooding phenomenon in packed columns. As such, the slight flooding phenomenon can be predicted, and the operational conditions of the packed columns can be adjusted in time. Accordingly, the flooding phenomenon can be prevented. The method according to the present disclosure does not need a great number of empirical parameters, can be applied to various types of packed columns, and does not rely on human judgment. Therefore, the method according to the present disclosure is extremely practicable in industry.

Although the present disclosure has been described in considerable detail with reference to certain embodiments thereof, other embodiments are possible. Therefore, the spirit and scope of the appended claims should not be limited to the description of the embodiments contained herein.

It will be apparent to those skilled in the art that various modifications and variations can be made to the structure of the present disclosure without departing from the scope or spirit of the disclosure. In view of the foregoing, it is intended that the present disclosure cover modifications and variations of this disclosure provided they fall within the scope of the following claims.

What is claimed is:

1. A method of real-time prognosis of a flooding phenomenon in a packed column, comprising:
   conducting an online data collection step, wherein a plurality of values of a pressure drop are collected from the packed column under operation;
   conducting a calculation step, wherein the values of the pressure drop are used to calculate a plurality of values of a steadiness index;
   conducting a statistical step, wherein a value of a monitoring statistic is calculated based on the values of the steadiness index; and
   conducting a control step, wherein the value of the monitoring statistic is compared to a control limit, and an alarm is triggered when the value of the monitoring statistic is greater than the control limit; and
   conducting an adjusting step after the alarm is triggered, wherein an operational condition of the packed column is adjusted to make the value of the monitoring statistic less than the control limit;
   wherein each of the values of the steadiness index is calculated by Formula (1), Formula (2) and Formula (3):

$$S^2 = \frac{\sum_{i=1}^{n}(P_i - \bar{P})^2}{n-1}; \quad (1)$$

$$\frac{\delta^2}{2} = \frac{\sum_{i=1}^{n-1}(P_{i+1} - P_i)^2}{2(n-1)}; \quad (2)$$

$$R = \frac{2S^2}{\delta^2}; \quad (3)$$

wherein R is the steadiness index, $S^2$ is an estimator of a sample variance, $\delta^2/2$ is another estimator of the sample variance, $P_i$ is an ith value of the pressure drop, n is a sample size of the values of the pressure drop, $\bar{P}$ is a sample mean of the values of the pressure drop with the sample size of n, and i is an integral from 1 to n.

2. The method of real-time prognosis of the flooding phenomenon in the packed column of claim 1, wherein the online data collection step is implemented by measuring the values of the pressure drop and delivering the values of the pressure drop to a computer via a sensing and transmitting element installed in the packed column, and the values of the pressure drop are recorded by the computer.

3. The method of real-time prognosis of the flooding phenomenon in the packed column of claim 2, wherein the packed column further comprises a blower and a liquid pump, and the blower changes a gas flow rate and/or the liquid pump changes a liquid flow rate according to an instruction of the computer.

4. The method of real-time prognosis of the flooding phenomenon in the packed column of claim 1, wherein the values of the pressure drop used in the calculation step is selected by a method of moving a time widow online.

5. The method of real-time prognosis of the flooding phenomenon in the packed column of claim 4, wherein a size of the time window is 20, and a step length of the time window is 1.

6. The method of real-time prognosis of the flooding phenomenon in the packed column of claim 1, wherein the value of the monitoring statistic and the control limit are obtained by a nonparametric statistical process control (SPC) method.

7. The method of real-time prognosis of the flooding phenomenon in the packed column of claim 6, wherein the nonparametric SPC method is a nonparametric SPC method using Mann-Whitney test.

8. The method of real-time prognosis of the flooding phenomenon in the packed column of claim 1, wherein, in the control step, the value of the monitoring statistic and the control limit are plotted in a control chart.

9. A method of real-time prognosis of the flooding phenomenon in a packed column, comprising:
   conducting an online data collection step, wherein a plurality of values of the pressure drop are collected from the packed column under operation;
   conducting a calculation step, wherein the values of the pressure drop are used to calculate a value of a steadiness index; and
   conducting a control step, wherein the value of the steadiness index is compared to a control limit, and an alarm is triggered when the value of the steadiness index is greater than the control limit; and
   conducting an adjusting step after the alarm is triggered, wherein an operational condition of the packed column is adjusted to make the value of the steadiness index less than the control limit;

wherein each of the values of the steadiness index is calculated by Formula (1), Formula (2) and Formula (3):

$$S^2 = \frac{\sum_{i=1}^{n}(P_i - \overline{P})^2}{n-1}; \quad (1)$$

$$\frac{\delta^2}{2} = \frac{\sum_{i=1}^{n-1}(P_{i+1} - P_i)^2}{2(n-1)}; \quad (2)$$

$$R = \frac{2S^2}{\delta^2}; \quad (3)$$

wherein R is the steadiness index, g is an estimator of a sample variance, $\delta^2/2$ is another estimator of the sample variance, $P_i$ is an ith value of the pressure drop, n is a sample size of the values of the pressure drop, $\overline{P}$ is a sample mean of the values of the pressure drop with the sample size of n, and i is an integral from 1 to n.

10. The method of real-time prognosis of the flooding phenomenon in the packed column of claim 9, wherein the online data collection step is implemented by measuring the values of the pressure drop and delivering the values of the pressure drop to a computer via a sensing and transmitting element installed in the packed column, and the values of the pressure drop are recorded by the computer.

11. The method of real-time prognosis of the flooding phenomenon in the packed column of claim 10, wherein the packed column further comprises a blower and a liquid pump, and the blower changes a gas flow rate and/or the liquid pump changes a liquid flow rate according to an instruction of the computer.

12. The method of real-time prognosis of the flooding phenomenon in the packed column of claim 9, wherein the values of the pressure drop used in the calculation step is selected by a method of moving a time widow online.

13. The method of real-time prognosis of the flooding phenomenon in the packed column of claim 12, wherein a size of the time window is 20, and a step length of the time window is 1.

14. The method of real-time prognosis of the flooding phenomenon in the packed column of claim 9, wherein the control limit is obtained by a nonparametric SPC method.

15. The method of real-time prognosis of the flooding phenomenon in the packed column of claim 14, wherein the nonparametric SPC method is a nonparametric SPC method using kernel density estimation.

16. The method of real-time prognosis of the flooding phenomenon in the packed column of claim 9, wherein, in the control step, the value of the steadiness index and the control limit are plotted in a control chart.

* * * * *